US012691207B2

(12) United States Patent
Srinivas et al.

(10) Patent No.: US 12,691,207 B2
(45) Date of Patent: Jul. 28, 2026

(54) PORTABLE DIALYSATE GENERATOR

(71) Applicant: TDA Research, Inc., Wheat Ridge, CO (US)

(72) Inventors: Girish Srinivas, Broomfield, CO (US); Edward B. Metcalf, Denver, CO (US); Allison M. Robinson, Arvada, CO (US); Joseph Leslie Fredrickson, Denver, CO (US); Nathan Weinstein, Golden, CO (US); Frank McCoy, Longmont, CO (US)

(73) Assignee: TDA Research, Inc., Golden, CO (US)

( * ) Notice: Subject to any disclaimer, the term of this patent is extended or adjusted under 35 U.S.C. 154(b) by 333 days.

(21) Appl. No.: 18/649,373

(22) Filed: Apr. 29, 2024

(65) Prior Publication Data

US 2025/0332330 A1 Oct. 30, 2025

(51) Int. Cl.
    *A61M 1/16* (2006.01)
    *A61M 1/26* (2006.01)
    *A61M 39/22* (2006.01)

(52) U.S. Cl.
    CPC .......... *A61M 1/1672* (2014.02); *A61M 1/167* (2014.02); *A61M 1/267* (2014.02); *A61M 39/223* (2013.01)

(58) Field of Classification Search
    CPC .... A61M 1/167; A61M 1/1672; A61M 1/267; A61M 39/223
    See application file for complete search history.

(56) References Cited

U.S. PATENT DOCUMENTS

| | | | |
|---|---|---|---|
| 5,951,863 | A | 9/1999 | Kruger et al. |
| 9,498,752 | B2 | 11/2016 | Park |
| 10,632,242 | B2 | 4/2020 | Caluya et al. |
| 2014/0319056 | A1 | 10/2014 | Fuchigami et al. |
| 2017/0065762 | A1* | 3/2017 | Larsen .............. B01D 61/0022 |
| 2021/0128807 | A1 | 5/2021 | Poppe et al. |
| 2022/0410073 | A1 | 12/2022 | Hotta |
| 2023/0054094 | A1 | 2/2023 | He et al. |
| 2023/0233994 | A1 | 7/2023 | Werner et al. |

FOREIGN PATENT DOCUMENTS

| | | |
|---|---|---|
| DE | 102020106751 | 8/2021 |
| EP | 3273275 | 1/2018 |
| EP | 4124377 | 2/2023 |
| WO | 2009083011 | 7/2009 |
| WO | 2014128293 | 8/2014 |

* cited by examiner

*Primary Examiner* — Dirk R Bass
(74) *Attorney, Agent, or Firm* — Sarah Hill; Brian Elliott

(57) ABSTRACT

A man-portable dialysate generator with a forward osmosis membrane module, a concentrated aqueous salt solution reservoir, a non-sterile water feedstock inlet, and a collection reservoir that produces sterile dialysate from non-sterile feed water. The dialysate generator does not have an electric-powered pump to move fluids across the osmosis membrane, or does not have electric-powered pumps that generate more than 5 psi for fluid pressure. The dialysate generator is man-portable, less than 50 pounds and maybe less than 31 pounds, and preferably less than 10 pounds. The device is particularly advantageous for use in forward deployed military patient care, disaster response or remote medical care situations away from clean water and electricity.

30 Claims, 25 Drawing Sheets

PORTABLE DIALYSATE GENERATOR

STATEMENT REGARDING FEDERALLY SPONSORED RESEARCH OR DEVELOPMENT

This invention was made using U.S. government funding through the U.S. Defense Health Agency, US Army Medical Research Acquisition Activity (USAMRAA), Small Business Innovation Research (SBIR) contract No. W81XWH-21-P-0012. The government has certain rights in this invention.

FIELD OF THE INVENTION

The technical field generally relates to portable generators to produce dialysate using a concentrated dialysate along with non-sterile water.

BACKGROUND

The treatment of medical patients requiring dialysate solution in off-the-grid, military, disaster, or wilderness situations is challenging because of the logistical burdens of transporting liquids to those theaters and also because power may not be available to run existing dialysate solution generators. For example, acute kidney injury (AKI) is a common complication of severe trauma and causes increased rates of morbidity and mortality even in patients who survive their initial life-threatening injuries. This response happens quickly, within 30 minutes of a major injury, and therefore it is important to begin addressing it before additional complications arise. It is critical for these patients to have rapid access to dialysis equipment, but battlefield hospitals and far-forward deployed surgical teams in remote response areas may be unable to access the large volumes of dialysate fluid required (75 L per patient per day). These large volumes of fluid are expensive and difficult to ship, and rely on a supply system that may be subject to interruption by disasters, interdiction, and attack. In these situations, it would be advantageous to produce dialysate on-demand in the field using locally available water sources.

Existing dialysate generators suffer from one of the following limitations: (1) they are large and difficult or impractical to move (i.e. they are not man-portable), (2) they are intended for use in a fixed production facility that then delivers whole dialysate in liquid bags/containers; (3) they require power to pump liquids for either fluid transfer, fluid dosing, or fluid pressurization, especially for reverse osmosis; (4) they require other bulky, powered reverse osmosis equipment to first purify water; (5) they require a sterile water feedstock; or, (6) they require equipment to measure the concentration of dialysate produced and complicated systems to adjust the final concentration.

Whole dialysate is produced in large pharmaceutical manufacturing facilities and typically supplied in 5 L quantities. A single patient being treated for hyperkalemia may require up to 15 bags per day (75 L/day). Hemodialysis patients can require up to 170 L/day. The logistics of delivering this quantity of useable dialysis fluid on a regular basis is extremely difficult (if not impossible) in the remote, disaster response, or military treatment scenarios.

On-site dialysate production requires advanced water filtration devices and dialysate concentrates to mix and form the whole solution just before administering dialysis. To avoid shipping whole dialysate, clinic and home-based dialysate generator systems have been developed. Although these systems can be moved, they are delivered by a truck or van and generally roll on wheels or a cart (not small enough to be carried by hand). These systems use energy intensive filtration methods to produce clean water meeting medical standards from municipal water. Typically, these systems rely on reverse osmosis (RO) units to purify and sterilize potable/municipal water. RO is a high pressure (100 s to 1000 s of psi), energy intensive process in which water is forced against the natural concentration gradient through a membrane to separate pure water from any contaminants. These systems require a large amount of power (100 V at 60 Hz) and significant potable water supplies.

U.S. Pat. No. 5,951,863A teaches reverse osmosis for producing medical grade water, and by extension solutions requiring medical grade water (water purification using reverse osmosis device for formulation of medical solution). U.S. Pat. No. 5,951,863A teaches a device for purifying fluids and in particular to a reverse osmosis device for use, for example, in sterilizing and purifying fluids serially through at least two reverse osmosis stages, for use in a system for medical drug formulation and delivery and for other end use applications. Most RO systems for dialysate production, in general, require around 10 liters of potable water for every liter of dialysate produced. Furthermore, the most "portable" versions of these systems are still bulky and heavy (around 60 lbs. or more). High-pressure vessels require steel vessels capable of holding several thousand pounds per square inch, thus setting a limit on how light-weight these devices can be.

The characteristics of existing dialysate generators, even those that can be moved on wheels or on a cart, make them impractical and unworkable in austere locations where access to high voltage power, large volumes of potable water, and transportation is limited or non-existent. Existing prior art does not teach or provide any effective man-portable solutions to this problem and there are technical reasons why existing systems cannot be adopted for smaller/lighter units or dialysate generators that are man-portable and that do not require electrical or external power.

Forward osmosis is another way to purify dirty water and form a sterile, albeit saline, solution. Dirty water can be exposed to one side of a forward osmosis membrane where the other side contains a sterile concentrated solution of ions (salts). Water molecules will then diffuse across the forward osmosis membrane and dilute the sterile concentrated side, thus forming a larger volume of sterile water-salt solution. For example, WO2014128293A1 teaches a water extraction system comprising a flow cell comprising a membrane; said membrane comprising an active layer comprising immobilized aquaporin water channels and a support layer, and said membrane having a feed side and a non-feed side; and an aqueous source solution in fluid communication with the feed side of the membrane. This device can be applied to use for removal of contaminants from water sources, for generation of diluted nutrient solutions for irrigation purposes using fertilizer drawn forward osmosis, or for process water treatment including extraction of water from used dialysate solutions.

Forward osmosis has further been used in other devices to processes dialysate. WO2009083011A3 teaches a forward osmosis (FO) membrane separation technique for dialysate regeneration. Regeneration is the recovery of water from used dialysate (not fresh/new dialysate). WO2009083011A3 teaches a forward osmosis process that has been used to extract a substantial portion of the water content of the spent dialysis fluid by simple (forward) osmosis in which water is extracted down a concentration gradient to dilute a concentrated electrolyte solution then by reverse osmosis in which more water is extracted and used to further dilute the concentrate to obtain a regenerated dialysis fluid. WO2009083011A3 teaches the use of pumps and fresh exogenous water. It does not teach a device to produce fresh dialysate from non-potable water, rather a portable device to recover water from used dialysate.

DE102020106751B4 teaches a device and method for producing dialysate, wherein the device comprises a first part and a second part formed as the circuit, wherein the first part comprises a water connection or a water tank and the primary side of a filter, the filter formed is to produce water purified from the water through forward osmosis, and wherein the second part of the secondary side of the filter, a reservoir, a filtrate line, which leads from the secondary side of the filter to the reservoir, and one of the reservoir to the secondary side of the filters leading return line comprises, further provided with an electrodialysis unit having a diluent chamber and a concentrate chamber, the concentrate chamber being in fluid communication with the secondary side of the filter. DE102020106751B4 teaches a device that requires both pumps and an electrodialysis unit operation to produce dialysate from a water source and a dialysate concentrate. DE102020106751B4 teaches away from a non-powered man-portable device that could produce fresh dialysate and also teaches away from a forward osmosis dialysate generator that can operably function with no power to purify the higher salt concentration side of the forward osmosis membrane.

Other existing methods or devices for producing dialysate from dirty water require other energy-intensive unit operations, like cryopurification of the water. EP3272375A1 (Goldau, 2016). EP3272375A1 teaches an apparatus for generating dialysate for dialysis comprising a dialysate outlet and a dialysate inlet and dialysate purifying means, wherein the purifying means comprise a cryopurifier for generating pure water, wherein the inlet of the cryopurifier is connected to the dialysate outlet and the outlet of the cryopurifier is connected to the dialysate inlet. The invention also relates to a method for reclaiming of fresh dialysate from ultrafiltrate and wasted dialysate extracted from a dialysis patient, comprising the following steps: (a) preparing an ice slurry from the dialysate, wherein the ice slurry contains ice crystals and a liquid containing solutes; and (b) separating the ice crystals from the liquid containing the solutes. EP3272375A1 fails to teach a non-powered device to produce dialysate from impure water using forward osmosis and no power to transfer the dialysate product. EP3272375A1 also teaches away from the unpowered production of dialysate from impure water by teaching the importance of cryopurification (i.e. low temperature freezing) to produce sterile clean water from the dirty water source.

The prior art fails to teach critical combinations of embodiments to enable a man-portable dialysate generator that can function on non-potable water, and requires no power to purify the produced dialysate, or to neither pump nor purify the produced dialysate.

BRIEF DESCRIPTION OF THE INVENTION

The present invention solves the limitations of the prior art and provides a man-portable dialysate generator that can use non-potable, non-sterile, raw, or untreated water feedstocks, combined with a forward osmosis membrane module and a dialysate concentrate feedstock to produce dialysate. The dialysate generator of the disclosure may require no electrical power to transfer dialysate product from the forward osmosis membrane module into a collection reservoir. It requires no external electrical power for complete sterilization of feed water and formation of medical grade dialysate solution. The dialysate generator of the disclosure may require or have no electrical power to pump or transfer liquid across the forward osmosis membrane (which is generally a very high power-consuming and high pressure step in the prior art), but may optionally use, have or require electrical power to move liquids in other parts of the device (and generally pumped at low pressures, for example less than 20 psi, less than 15 psi, less than 10 psi, or less than 5 psi.) The module is rated to 30 psi, so pressure on the sterile side (past the forward osmosis membrane) may be 30 psi, less than 30 psi, less than 25 psi, less than 22 psi, less than 20 psi, less than 15 psi, less than 10 psi, or less than 5 psi. Pressure on the sterile side may be about 0 psi or just greater than 0 psi when the device has not been in use. The pressure on the feed side is limited by gravity or a feed pump pressure, and may be less than 10 psi, less than 8 psi, less than 5 psi, or less than 3 psi. The feed side may go into a vacuum state which may be up to 10 psi vacuum, up to 8 psi vacuum, up to 5 psi vacuum, up to 3 psi vacuum.

In an embodiment, the portable dialysate generator comprises: a forward osmosis membrane module (101); a concentrated aqueous salt solution reservoir (102); a non-sterile water feedstock inlet (103); and, a collection reservoir (104). The forward osmosis membrane module has a first fluid side (105) and a second fluid side (106), the first fluid side and the second fluid side being separated by an osmosis membrane (107); the non-sterile water feedstock inlet is operably connected to, and in fluid communication with the first fluid side of the forward osmosis membrane module; the concentrated aqueous salt solution reservoir is operably connected to, and in fluid communication with the second fluid side of the forward osmosis membrane module; the collection reservoir is operably connected to, and in fluid communication with the second fluid side of the forward osmosis membrane module; the portable dialysate generator does not have an electric-powered pump to move a fluid across the osmosis membrane; and, the portable dialysate generator is man-portable.

Alternatively, the disclosure provides a portable dialysate generator comprising: a forward osmosis membrane module; a concentrated aqueous salt solution reservoir; a non-sterile water feedstock inlet; and, a collection reservoir. The forward osmosis membrane module has a first fluid side and a second fluid side, the first fluid side and the second fluid side being separated by an osmosis membrane; the non-sterile water feedstock inlet is operably connected to, and in fluid communication with the first fluid side of the forward osmosis membrane module; the concentrated aqueous salt solution reservoir is operably connected to, and in fluid communication with the second fluid side of the forward osmosis membrane module; the collection reservoir is operably connected to, and in fluid communication with the second fluid side of the forward osmosis membrane module; the portable dialysate generator does not have an electric-powered pump that generates more than 5 psi for fluid pressure (facilitates directing of fluid components, but does not provide sufficient pressure to overcome the pressure requirements to drive fluid across the forward osmosis membrane); and, the portable dialysate generator is man-portable.

In an optional embodiment, the dialysate generator does not have an electric-powered pump to move a non-sterile water feedstock through the non-sterile water feedstock inlet into the forward osmosis membrane module; and the portable dialysate generator does not have an electric-powered pump to move a concentrated aqueous salt solution from the concentrated aqueous salt solution reservoir into the forward osmosis membrane module.

In a preferred embodiment, the non-sterile water feed-stock inlet and the concentrated aqueous salt solution reservoir are operably connected to the forward osmosis membrane module in a counter-concurrent configuration.

In an optional embodiment, the dialysate generator further comprises a non-sterile water feedstock reservoir (108) operably connected to and in fluid communication with the non-sterile water feedstock inlet, wherein, the non-sterile water feedstock source is mounted above the forward osmosis membrane module, operably allowing gravity-feeding of fluid from the non-sterile water feedstock source into the forward osmosis membrane module. In another optional embodiment, the dialysate generator further comprises a non-sterile water feedstock source (508) and a feed pump (570), wherein the feed pump is connected between and in fluid communication with the non-sterile water feedstock source and the non-sterile water feedstock inlet, operably allowing on-demand pumping of fluid from the non-sterile water feedstock source into the forward osmosis membrane module. Optionally, the dialysate generator further comprises an injection concentrate pump (560), wherein, the injection concentrate pump is connected between the concentrated aqueous salt solution reservoir and the forward osmosis membrane module, and is operably connected to and in fluid communication with the concentrated aqueous salt solution reservoir and the forward osmosis membrane module, operably allowing on-demand pumping of fluid from the concentrated aqueous salt solution reservoir into the forward osmosis membrane module.

In an embodiment, the portable dialysate generator further comprises a sterile dialysate collection reservoir; wherein, the sterile dialysate collection reservoir is connected to and in fluid communication with the second fluid side of the forward osmosis membrane module. The sterile dialysate collection reservoir may be fillable by a produced dialysate from the second fluid side of the forward osmosis membrane module, and wherein there is no electric-powered pump to move the produced dialysate from the forward osmosis membrane module to the sterile dialysate collection reservoir. The sterile dialysate collection reservoir may be either a flexible and fillable bag or a movable piston, and the sterile dialysate collection reservoir may be operably connected to the forward osmosis membrane module so excess fluid volume produced in the forward osmosis membrane module can fill the sterile dialysate collection reservoir.

In an embodiment of the portable dialysate generator wherein the collection reservoir comprises a two-stroke piston with a first collection reservoir side and a second collection reservoir side, the portable dialysate generator further comprises a four-way valve. The four-way valve is operably connected to and in fluid communication with the forward osmosis membrane module and the collection reservoir; and, the four-way valve directs fluid communication from the forward osmosis membrane module to the first collection reservoir side or to the second collection reservoir side.

The portable dialysate generator may further comprise a final dialysate product collection reservoir, wherein, the two-stroke piston is operably connected to the four-way valve and the final dialysate product collection reservoir such that when the four-way valve is positioned so that excess fluid volume from the forward osmosis membrane module is directed to the first collection reservoir side, the produced dialysate in the second collection reservoir is dispelled into the final dialysate product collection reservoir; and wherein, the two-stroke piston is operably connected to the four-way valve and the final dialysate product collection reservoir such that when the four-way valve is positioned so that excess fluid volume from the forward osmosis membrane module is directed to the second collection reservoir side, the produced dialysate in the first collection reservoir is dispelled into the final dialysate product collection reservoir. Optionally, the final dialysate product collection reservoir comprises a bag reservoir with a first compartment and a second compartment, wherein the first compartment and the second compartment are separated by a frangible seal, wherein the produced dialysate is dispelled into the first compartment, and wherein an additive is stored, either as a solid or liquid, in the second compartment.

In an optional embodiment, the portable dialysate generator further comprises at least one of a microfilter, a particle pre-filter, or an activated carbon filter operably connected to and in fluid communication between the non-sterile water feedstock source and the non-sterile water feedstock inlet. Optionally, the dialysate generator further comprises an ion exchange resin operably connected to and in fluid communication between the non-sterile water feedstock source and the at least one of the microfilter, the particle pre-filter, or the activated carbon filter.

Optionally, the portable dialysate generator may further comprise a backflush and sterilization reservoir; and, a sterilization pump; wherein, the backflush and sterilization reservoir is operably connected to and in fluid communication with the first fluid side of the forward osmosis membrane module; wherein, the sterilization pump is operably connected to and in fluid communication between the backflush and sterilization reservoir and the forward osmosis membrane module; and, wherein, the sterilization pump operably allows on-demand pumping of fluid from the backflush and sterilization reservoir into the forward osmosis membrane module. The portable dialysate generator may further comprise a particle pre-filter, wherein the backflush and sterilization reservoir is further operably connected to and in fluid communication with the particle pre-filter.

In an embodiment, the portable dialysate generator further comprises an acid reservoir and an acid pump. The acid reservoir is operably connected to and in fluid communication between the forward osmosis membrane module and the sterile dialysate collection reservoir; the acid pump is operably connected to and in fluid communication between the acid reservoir and the sterile dialysate collection reservoir; the acid pump allows for on-demand pumping of fluid from the acid reservoir to the produced dialysate from the forward osmosis membrane module before entering the sterile dialysate collection reservoir; and the acid pump does not move fluid from the forward osmosis membrane module to the sterile dialysate collection reservoir.

In an optional embodiment, the portable dialysate generator further comprises a pressure relief valve connected to and in fluid communication with the second fluid side of the forward osmosis membrane module. The pressure relief valve may be further connected to and in fluid communication with the first fluid side of the forward osmosis membrane module, allowing flow from the second fluid side to the first fluid side to relieve pressure.

In an optional embodiment, the dialysate generator further comprises a bypass valve and a discharge reservoir, wherein the bypass valve is operably connected and in fluid communication with the second fluid side of the forward osmosis membrane module and the discharge reservoir.

In optional embodiments the reservoir is a bag reservoir containing frangible seal to add bicarbonate after a latent period of storage. This "frangible seal" is used to add the $2^{nd}$ part of a 2-part dialysis solution, either in solid or liquid form, to the $1^{st}$ part of the dialysis solution, produced on the generator, prior to use in a dialysis machine or patient. A non-limiting example is adding bicarbonate back in for a 2-part dialysis solution composed of a bicarbonate buffer and an acid/electrolyte solution. A reason to do this is that with the 2-part solutions (like with bicarbonate) there is typically a precipitation reaction ($CaCO_3$ and $MgCO_3$), which is why they can't be stored as a single solution. In an embodiment the bag has a first compartment where the produced dialysate flows into, and a second compartment where the second part of the dialysate is stored, either as a solid or a liquid and a seal, which can be broken to mix the two compartments. The bag reservoir may further comprise a third compartment also separated by a frangible seal and containing acid, either as a solid or a liquid, for pH adjustment.

DETAILED DESCRIPTION OF THE INVENTION

Figure 1:
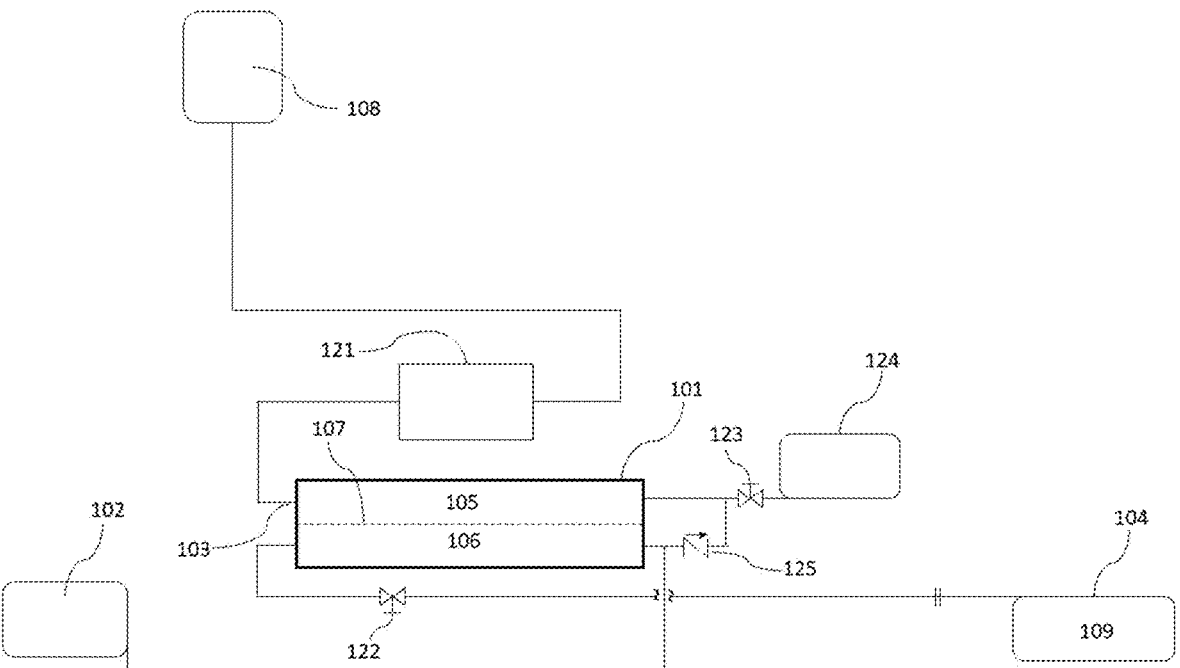
FIG. 1: Schematic of the portable dialysate generator.

The present invention provides a portable dialysate generator that requires no electrical power to transfer liquid across the forward osmosis membrane, and has optional battery-operated components for low-pressure pumping feed water, injection concentrate, acid pH adjustment, and/or sterilized backflush into the system for continuous, autonomous operation. The feed pump may pump liquid at up to 5 psi, up to 4 psi, up to 3 psi, up to 2 psi, or up to 1 psi. The injection concentrate pump may operate at up to 30 psi, up to 25 psi, up to 22 psi, up to 20 psi, up to 18 psi, up to 15 psi, up to 12 psi, or up to 10 psi. None of the pumps generate more than 5 psi at the forward osmosis membrane surface, meaning that the injection concentrate pump may operate at a higher driving pressure to overcome the pressure generated by the forward osmosis membrane. It is light weight (for example less than 50 lbs, less than 40 lbs, less than 30 lbs, less than 25 lbs, less than 20 lbs., less than 18 lbs., less than 16 lbs., less than 14 lbs., less than 12 lbs., less than 10 lbs., less than 8 lbs., less than 6 lbs., or less than 4 lbs.). In a non-limiting example, the generator includes all possible battery-operated pumps for autonomously regulating the flow of external components into the generator, and is about 24 to 26 lbs. In a non-limiting example the generator does not include any battery-operated pumps and is about 5 to 6 lbs. For ease of transport, the device may be stored in a portable hard case, a non-limiting example is an 11.5 lb., 20.66×17.20×8.40 inch exterior hard case (total weight of 17.3 lbs. for the case and a 5.8 lb. device). This eliminates issues with cube and weight of alternative devices (RO based units).

The present invention overcomes a significant limitation of RO based technology (power consumption) by requiring no external power for generating the high pressure required. It can use any locally available water and concentrated dialysate to produce sterile bags of dialysate at the required concentration. This eliminates the need for large potable water supplies, and simply requires a non-potable water source near the point of care. Although powered pumps could be used to meter in the dialysate concentrate, they are not required and in all instances there is no power required to move the produced dialysate from the forward osmosis membrane module to the collection. There is also no electrical power required to further purify or adjust the concentration of the dialysate that is produced in the forward osmosis membrane module prior to storage in the reservoir and patient use. There is no power used to move the dialysate from the module, and there is no need to pump it through any additional features. This feature overcomes the limitations of existing forward osmosis devices that are directed toward dialysate recycle or production, and that require power to move or purify the dialysate. These added requirements add the need for both more weight and cube and also the logistical burden of requiring electricity.

The present invention teaches a man-portable dialysate generator that uses a concentrate which may be introduced in a ratio of 40 mL of concentrate for each L of produced dialysate (25:1 volume reduction), reducing the shipped volume (and cube) of dialysate fluids by 96%. Other volume ratios may be 50:1, 40:1, 30:1, 20:1, and 15:1. The starting concentration of the concentrated dialysate is selected and identified in the present invention to enable the FO module to correctly function to produce dialysate in reasonable time and without generating excess pressure that would damage the FO module. The contact time (also called the "run time") taught by the present invention is less than 4 hours, less than 2 hours and preferably less than 1 hour. The contact time maybe at least 4 minutes and at most 10 minutes, or alternatively about 20 minutes. The produced dialysate concentration is achieved by selection of the injection concentrate, and design of the system filling mechanism. The system may optionally be outfitted with in-line conductivity meters, or a digital dialysate meter to measure samples of the produced dialysate. This device can provide verification of dialysate quality but is not required to build an operable dialysate generator. It should be understood that having batteries operate on quality-checking components does not equate to having a powered system, or a partially-powered system that has a non-powered osmosis process or osmosis module, which relies on an external power source or frequent charging.

The dialysate generator of the present disclosure can use any fresh water source (potable or non-potable) and purify it to produce water for hemodialysis. In an embodiment, the dialysate generator of the present disclosure comprises an ion exchange resin so it can use any salty water source in addition to any fresh water source. This water dilutes the dialysate concentrate to produce the desired dialysate. The purity of the dialysate may optionally be verified using water quality analysis following ISO 23500-5:2019. In an aspect, the invention is a device that requires no electrical power, is very lightweight (for example less than 10 lbs. or less than 7 lbs.), and is easily portable to remote areas for on-demand production of dialysate.

In the Specification and the accompanying Claims, the following terms are given their plain meaning as well as the additional meanings written below.

The term "portable" or "man-portable" means being capable of being carried by one man or person (non-gender specific). The upper weight limit may be approximately 14 kilograms (31 pounds). Optionally, man-portable may mean from 26 to 50 pounds. It may also mean equipment which can be carried by one man or person (gender non-specific) over long distance without serious degradation of the performance of normal duties.

The term "forward osmosis membrane module" means a membrane and housing the has an osmosis membrane separating two liquid wetted sides. The sides may be feed and permeate, retentate and permeate or other terms known in the art. The membrane may be a flat sheet, a spiral wound sheet, hollow fibers, or hollow tubes. The membrane module uses some form of seal to separate the two liquid sides, such as a tube sheet, or other sealing material. In certain instances, forward osmosis membrane modules are used in a water separation process that use the natural energy of osmotic pressure to separate water from dissolved solutes. The osmotic pressure is used to transport water through the membrane while retaining all dissolved solutes and/or pathogens on each side.

The term "concentrated aqueous salt solution reservoir" means a container with a solution of the salts and ionic species found in dialysate at a concentration that is higher than the final dialysate product concentration. The reservoir may be a flexible bag, a medical fluid bag, a polymer container, a collapsible container, or a container that allows fluid to empty without cavitating or developing a reduced pressure or vacuum.

The term "non-sterile water feedstock inlet" means a fluid connection opening or fitting to connect the feedstock water (non-sterile water feedstock source) with the forward osmosis membrane module. This can be a hose barb, a threaded fitting, an orifice, a funnel, or the like. The non-sterile water itself may be raw water from surface waters (creeks, lakes), raw ground water, used municipal waters, grey water, contaminated water, untreated rainwater, storm runoff water, or municipal water that is potable or non-potable.

The term "collection reservoir" means a container that can be filled with the produced dialysate. It may be a rigid container with a vent or a flexible container, such as a polymer bag, that can fill and expand.

The term "first fluid side" means a water-wetted side of the membrane module that contains the non-sterile water feedstock when in use.

The term "second fluid side" means a water-wetted side of the membrane module that contains the concentrated dialysate at the start of the run when the device is in use, and which becomes more diluted as water from the first fluid side permeates across the osmosis membrane. The mass transfer of water is from the first fluid side to the second fluid side. The second fluid side is the sterile side of the membrane.

The term "osmosis membrane" means a semipermeable membrane. The membrane can be used either for reverse osmosis (RO) or forward osmosis (FO). Examples of osmosis membranes include asymmetric skinned polymer membranes (with a thin solid skin), nanoporous polymer membranes, and skinned or nanoproous polymer membrane containing a hydrophilic surface coating to promote water permeation. Without wishing to be bound by theory, osmosis membranes may use solution-diffusion as the physical means of permeating water while preventing permeation of salts and bacteria, or they may use molecular sieving or Knudsen diffusion in nanoporous polymer to allow water to selectively permeate be a molecular size-exclusion mechanism. Non-limiting examples of materials used for osmosis membranes are cellulose acetate or polysulfone coated with aromatic polyamides. Certain osmosis membranes have a support web (such as polyester fibers), a microporous interlayer (such as polysulfone) and a thin solid skin layer on top (such as polyamide). Other nanostructured ceramic may be used as the osmosis membrane, non-limiting examples are zeolites. Osmosis membranes may be made from nano-structured polymers or microporous supports coated with a skin layer of nanoporous polymers.

Osmosis membrane may also mean membranes that are bio-mimetic and that have natural building blocks like lipids and artificial components such as block-copolymers or liquid crystals used to create membranes with water molecular channels, or water transport nano-channels. These biomimetic membranes may contain protein or stabilized protein derivatives or adducts. These biomimetic membranes may contain aquaporin protein or stabilized aquaporin protein derivatives or adducts.

The term "the non-sterile water feedstock source" means a water source that is not medical grade for injection or is not sterile for medical purposes. The non-sterile water may be relatively clean potable water, such as municipal drinking water, and it may be unclean water such as raw water from surface water sources like creeks, rivers, lakes. It may be raw ground water, grey waters, untreated rainwater, storm runoff water, municipal water that is treated or untreated. It may also contain ions, organics or pathogens. In certain aspects, it may be brackish or have an ionic strength higher than typical fresh water sources, yet lower than the ionic strength of the final dialysate product (so that forward osmosis is still possible). An ion exchange resin is required in embodiments using more saline waters. Although not wishing to be bound by theory, the non-sterile water feedstock is operable in the device of the present invention by enabling forward osmosis in the membrane module (i.e. the thermodynamic driving force is for water to permeate from the first fluid side to the second fluid side of the forward osmosis membrane module). The feedstock water may also be a water source that has an unknown purity and does not exclude water that is actually clean enough to be sterile, but is not known to be sterile by the operator. The device will operate with any of these water sources. The non-sterile water feedstock source may be in a container, maybe lifted above the device to allow for gravity flow, or it may be used from its original source and connected to the dialysate generator with tubing and a pump (i.e., the dialysate generator may be connected to a preexisting water faucet).

The term "electric-powered pump" means a pump, such as a water pump, or a dialysate pump that uses electricity to operate. The electricity may be supplied by direct connection to another power source (i.e. a building's 50-60 Hz, or 110 to 220 Volt, or other supply) or an external power supply, an internal or external battery, solar panels, fuels cells, and the like.

The term "produced dialysate" means a dialysate with the proper concentration of solutes and ready for patient use. The produced dialysate means a dialysate that was made by starting with a concentrated and sterile feed and diluting it with water that is produced by the forward osmosis of the device. The produced dialysate may or may not comprise additive components, such as acids or other ions.

The term "concentrated aqueous salt solution" means a solution of water and salt solutes that is more concentrated than whole dialysate. The concentrated aqueous salt solution also has a higher ionic strength than the non-sterile water feedstock (i.e. to promote forward osmosis).

The term "counter-current configuration" means the normal definition in the art. When two liquid water streams are contacted with each other (with a semipermeable membrane separating them, the two streams are introduced into the membrane module such that they flow in opposite directions. It also means that the non-sterile water feed enters on the side of the module where the produced dialysate exits the membrane module. In more complex geometries such as spiral wound modules this counter-current term is understood to have the same meaning with regard to where each fluid stream contacts the other (with the membrane between) even if the module has a geometry such that the inlet and outlet are not necessarily on opposite sides.

The term "non-sterile water feedstock reservoir" means a vessel, polymer bag, tank, hopper, funnel, and the like. The reservoir is any device that can hold water prior to allowing it to flow or be forced into the membrane module. The reservoir may be vented (open to atmosphere) to allow smooth water feeding, or it may be sealed, or even flexible or collapsible.

The term "feed pump" means a pump, which may be powered or hand-operated, that is connected between the non-sterile water feedstock reservoir or non-sterile water feedstock source and the forward osmosis membrane module and is operably connected to and in fluid communication with the non-sterile water feedstock (reservoir/source) and the forward osmosis membrane module, operably allowing on-demand pumping of fluid from the non-sterile water feedstock into the forward osmosis membrane. This should not be confused with the pump that is excluded from being present on the outlet of the second fluid side of the membrane module, which the exclusion of that pump is an embodiment of the present invention.

The term "injection concentrate pump" means a pump, which may be powered or hand-operated, that is connected between the concentrated aqueous salt solution reservoir and the forward osmosis membrane module and is operably connected to and in fluid communication with the concentrated aqueous salt solution reservoir and the forward osmosis membrane module, operably allowing on-demand pumping of fluid from the concentrated aqueous salt solution into the forward osmosis membrane. This should not be confused with the pump that is excluded from being present on the outlet of the second fluid side of the membrane module, which the exclusion of that pump is an embodiment of the present invention.

The term "backflush and sterilization reservoir" means a container with a solution of a concentrated sterilant mixed with microbe-free water. The solution must be capable of sterilizing the forward osmosis module, as well as any prefilters during a backflush process to remove contaminants or particulate matter.

The term "sterilization pump" means a pump, which may be powered or hand-operated, that is connected between the backflush and sterilization reservoir and the forward osmosis membrane module and is operably connected to and in fluid communication with the backflush and sterilization reservoir and the forward osmosis membrane module, operably allowing on-demand pumping of sterile solution into the forward osmosis membrane. It may also be operably connected to and in fluid communication with the prefilter, operably allowing on-demand pumping of sterile solution through the prefilter and into a discharge outlet/reservoir to remove any particles clogging the filter. This should not be confused with the pump that is excluded from being present on the outlet of the second fluid side of the membrane module, which the exclusion of that pump is an embodiment of the present invention.

The term "acid reservoir" means a container with a solution of concentrated acid, such as hydrochloric acid, capable of balancing the pH of the final dialysate product when sodium bicarbonate is added to the produced solution.

The term "acid pump" means a pump, which may be powered or hand-operated, that is connected between the acid reservoir and the collection reservoir and is operably connected to and in fluid communication with the acid reservoir and the collection reservoir, operably allowing on-demand pumping of acid into the produced dialysate prior to entering the collection reservoir or two-stroke piston. This should not be confused with the pump that is excluded from being present on the outlet of the second fluid side of the membrane module, which the exclusion of that pump is an embodiment of the present invention.

The term "sterile dialysate collection reservoir" means a vessel, polymer bag, tank, hopper, funnel, and the like. The reservoir is any device that can receive produce dialysate from the membrane module. The reservoir is operably sealed (to air and liquids) to maintain sterile conditions. It may allow smooth filling of the produced dialysate by expanding while being filled. It may be flexible or have and expandable piston.

The term "two-stroke piston" means a piston that has two sides and can combine two functions into one piston-movement; during the first direction movement of the piston the first side fills with liquid and the first chamber expands, while simultaneously fluid in the second side is expelled and the second chamber empties and collapses/closes. Conversely, during the second direction movement of the piston the second side fills with liquid and the second chamber expands, while simultaneously fluid in the first side is expelled and the first chamber empties and collapses/closes. A two-stroke piston may be a cylindrical piston where each side acts like a syringe, or it may be functional equivalents such as a rigid vessel with a flexible diaphragm separating two chambers.

The term "first collection reservoir side" means the first chamber of the two-stroke piston the fills with dialysate.

The term "second collection reservoir side" means the opposite side of the two-stroke piston as the first collection reservoir side. This side fills while the first side is being expelled/emptied.

The term "four-way valve" means a four-way valve, a four-way cock and is a fluid control valve whose body has four ports equally spaced round the valve chamber and the plug has two passages to connect adjacent ports. The plug may be cylindrical or tapered, or a ball. It has two flow positions, and usually a central position where all ports are closed. It can be used to isolate and to simultaneously bypass a sampling cylinder installed on a pressurized water line. It is useful to take a fluid sample without affecting the pressure of a hydraulic system and to avoid degassing (no leak, no gas loss or air entry, no external contamination).

The term "final dialysate product collection reservoir" means a collection reservoir that is in a form suitable for use on a patient needing dialysate. A non-limiting example is a medical fluid bag.

The term "pressure relief valve" means its ordinary meaning in the art. When the fluid pressure in the membrane module exceeds a pre-determined limit the normally closed relief valve opens to vent off excess liquid to avoid the pressure exceeding the limit.

The term "bypass valve" means its ordinary meaning in the art, creating an alternative flow path that bypasses the collection reservoir, two-stroke piston and four-way valve, and final collection reservoir and instead flows into a discharge outlet or discharge reservoir. The valve may be manual, or automated so a pre-determined amount of liquid passes through the valve (thereby not collecting in the collection reservoir) before closing and redirecting liquid (i.e., produced dialysate) to the normal flow path into the collection reservoir.

The term "frangible seal" means its ordinary meaning in the art. Frangible seal pouches are multiple-component packages used when components are separation until use. The frangible seal is easily broken with pressure applied by a user, allowing both sides of the frangible seal to mix.

Variations and features of the invention are further illustrated in the accompanying figures. FIG. 1 shows components and their connections for a portable dialysate generator having a forward osmosis membrane module (101); a concentrated aqueous salt solution reservoir (102); a non-sterile water feedstock inlet (103); and a collection reservoir (104). The forward osmosis membrane module has a first fluid side (105) and a second fluid side (106), the first fluid side and the second fluid side being separated by an osmosis membrane (107). The generator also has a non-sterile water feedstock inlet (103) that is operably connected to, and in fluid communication with the first fluid side of the forward osmosis membrane module. As shown in FIG. 1, there is no electric-powered pump to move a produced dialysate (109) from the forward osmosis membrane module into the collection reservoir (104). There is no power used to generate fluid pressure to drive flow across the forward osmosis membrane from the first fluid side (feed side) to the second fluid side (product side). The device in FIG. 1 is man-portable: it is less than 31 pounds, preferably at most 10 pounds. Also, the portable dialysate generator may have a non-sterile water feedstock (108), which may be a stagnant reservoir mounted above the forward osmosis membrane module, operably allowing gravity-feeding of fluid from the non-sterile water feedstock reservoir into the forward osmosis membrane module. In an optional embodiment shown in FIG. 1, the portable dialysate generator has a prefilter (121) between the non-sterile water feedstock and the forward osmosis membrane, removing larger contaminants from the non-sterile water before entering and potentially damaging the forward osmosis membrane. Optionally, there is a drain valve (123) to control the flow of the feed water through the forward osmosis membrane module, and the drain valve may be optionally connected to a feed waste discharge reservoir (124), and a recycling valve (125) that re-routes fluid from the sterile, second fluid side, to the feed, first fluid side, when there is pressure buildup. Optionally, there is also a product valve (122) to control the flow of sterile dialysate product from the second fluid side of the forward osmosis membrane to the collection reservoir.

Figure 2:
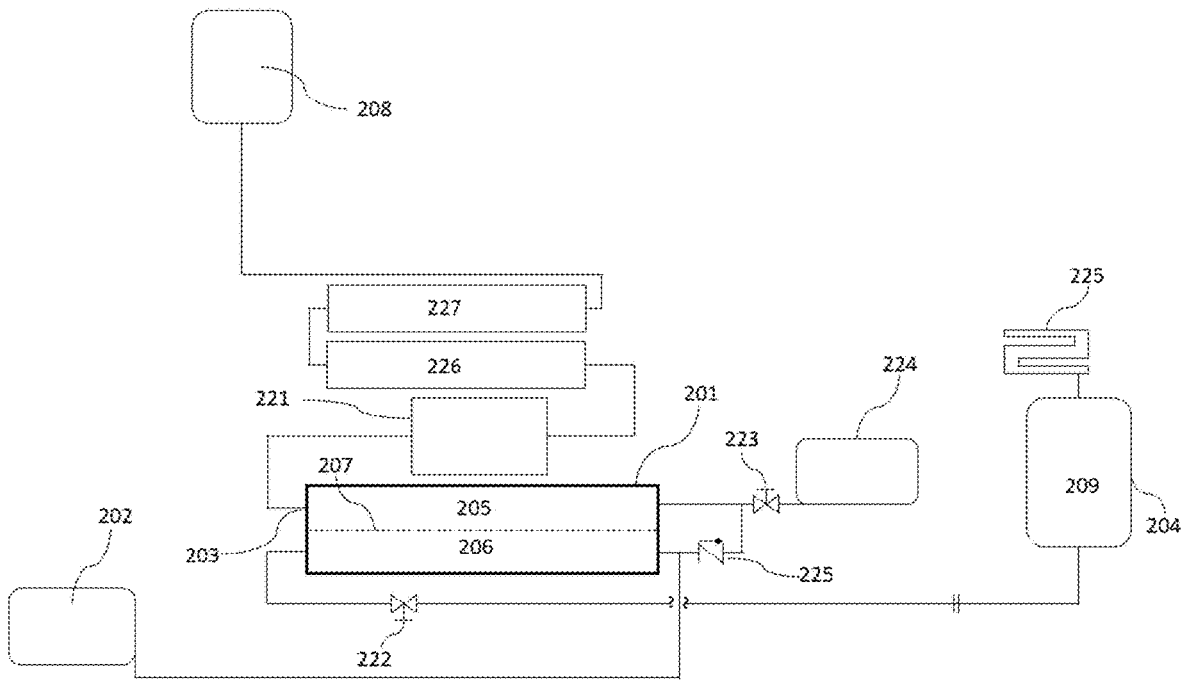
FIG. 2: Schematic of the portable dialysate generator with optional ion exchange resin, also optional connection to load cell.

FIG. 2 shows components and their connections for a portable dialysate generator having a forward osmosis membrane module (201); a concentrated aqueous salt solution reservoir (202); a non-sterile water feedstock inlet (203); and a collection reservoir (204). The forward osmosis membrane module has a first fluid side (205) and a second fluid side (206), the first fluid side and the second fluid side being separated by an osmosis membrane (207). Produced dialysate (209) is moved from the second fluid side to the collection reservoir (204), optionally with this flow controlled by a product valve (222). FIG. 2 shows the optional further connection of the collection reservoir to a load cell (225). The device in FIG. 2 is man-portable: it is less than 31 pounds, preferably at most 10 pounds. Also, the portable dialysate generator may have a non-sterile water feedstock (208), which may be a stagnant reservoir mounted above the forward osmosis membrane module, operably allowing gravity-feeding of fluid from the non-sterile water feedstock reservoir into the forward osmosis membrane module. The portable dialysate generator in FIG. 2 shows an optional prefilter (221) between the non-sterile feedstock and the first fluid side of the forward osmosis membrane, and a further optional carbon column (226), as well as an optional ion exchange resin (227) preceding the prefilter and expanding the non-sterile feedwater sources possible for sterilization to include salty water, among other sources. Optionally, there is a drain valve (223) to control the flow of the feed water through the forward osmosis membrane module, and the drain valve may be optionally connected to a feed waste discharge reservoir (224), and a recycling valve (225) that re-routes fluid from the sterile, second fluid side, to the feed, first fluid side, when there is pressure buildup.

Figure 3:
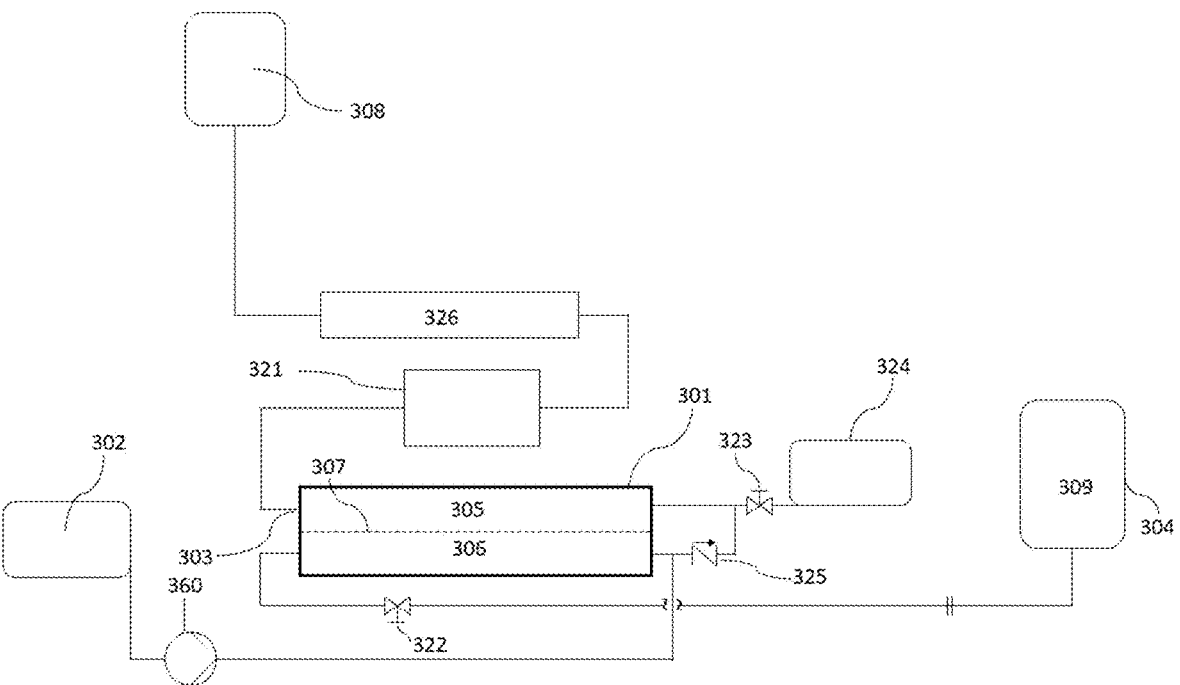
FIG. 3: Schematic of the portable dialysate generator with optional pump for injection concentrate.

FIG. 3. Shows components and their connections for a portable dialysate generator having a forward osmosis membrane module (301); a concentrated aqueous salt solution reservoir (302); a non-sterile water feedstock inlet (303); and a collection reservoir (304). The forward osmosis membrane module has a first fluid side (305) and a second fluid side (306), the first fluid side and the second fluid side being separated by an osmosis membrane (307). Produced dialysate (309) is moved from the second fluid side to the collection reservoir (304), optionally with this flow controlled by a product valve (322). There is no power used to generate fluid pressure to drive flow across the forward osmosis membrane from the first fluid side (feed side) to the second fluid side (product side). The device in FIG. 3 is man-portable: it is less than 50 pounds, preferably less than 31 pounds. Also, the portable dialysate generator may have a non-sterile water feedstock (308), which may be a stagnant reservoir mounted above the forward osmosis membrane module, operably allowing gravity-feeding of fluid from the non-sterile water feedstock reservoir into the forward osmosis membrane module. There is a carbon column (326) and a prefilter (321) preceding the forward osmosis membrane for further filtration of the non-sterile feedstock water. Optionally, there is a drain valve (323) to control the flow of the feed water through the forward osmosis membrane module, and the drain valve may be optionally connected to a feed waste discharge reservoir (324). There is a recycling valve (325) that re-routes fluid from the sterile, second fluid side, to the feed, first fluid side, when there is pressure buildup. The portable dialysate generator in FIG. 3 has an injection concentrate pump (360), which may be manual or automated, for controlling the flow of injection concentrate to the second fluid side of the forward osmosis membrane. As shown in FIG. 3, the collection reservoir is fillable by sterile dialysate produced on the second fluid side of the forward osmosis membrane module, and there is no electric-powered pump to move a fluid from the forward osmosis membrane module into the sterile dialysate collection reservoir. The sterile dialysate collection reservoir is either a flexible and fillable bag or is a movable piston, wherein the sterile dialysate collection reservoir is operably connected to the forward osmosis membrane module so that excess fluid volume that can be produced in the forward osmosis membrane module can fill the sterile dialysate collection reservoir.

Figure 4:
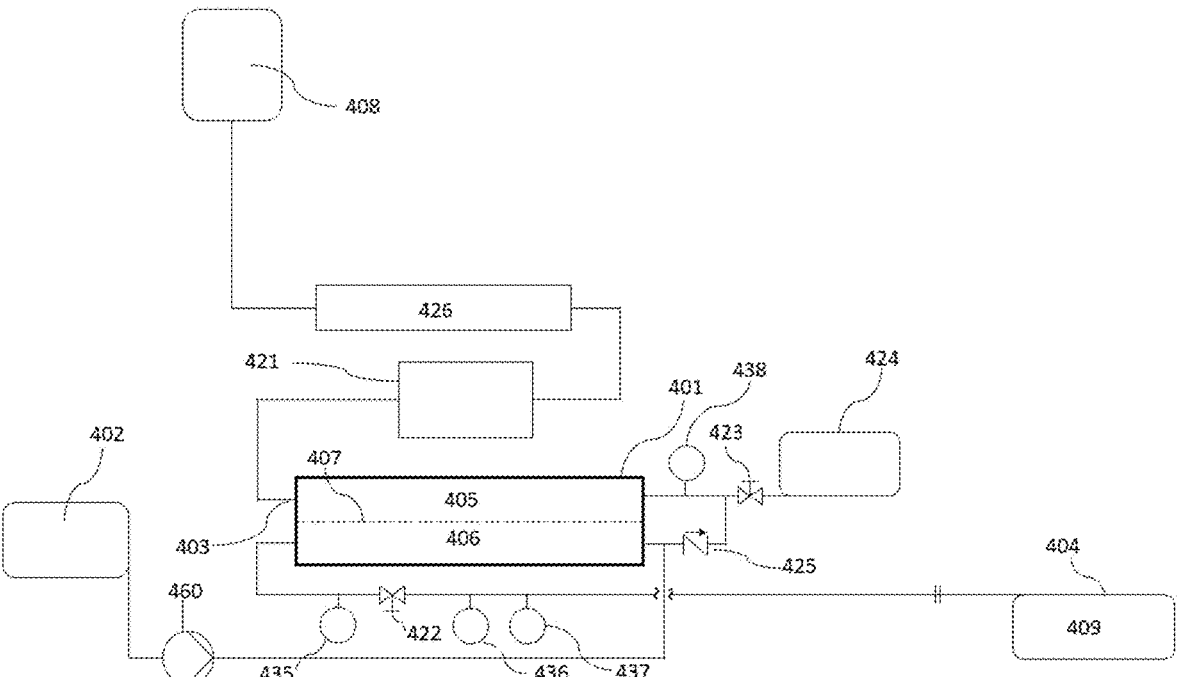
FIG. 4: Schematic of the portable dialysate generator with optional pump for injection concentrate, and optional transmitters.

FIG. 4. shows components and their connections for a portable dialysate generator having a forward osmosis membrane module (401); a concentrated aqueous salt solution reservoir (402); a non-sterile water feedstock inlet (403); and a collection reservoir (404). The forward osmosis membrane module has a first fluid side (405) and a second fluid side (406), the first fluid side and the second fluid side being separated by an osmosis membrane (407). Produced dialysate (409) is moved from the second fluid side to the collection reservoir (404), optionally with this flow controlled by a product valve (422). FIG. 4 also comprises a carbon column (426) and prefilter (421) before the non-sterile water feedstock inlet to the forward osmosis membrane, a drain valve (423) to control the flow of the feed water through the forward osmosis membrane module connected to a feed waste discharge reservoir (424), and a recycling valve (425) that re-routes fluid from the sterile, second fluid side, to the feed, first fluid side, when there is pressure buildup. FIG. 4 has an injection concentrate pump (460). FIG. 4 shows additional optional transducers, a product pressure transducer (435) before the product valve, a product flow transducer (436) and a product analyte transducer (437) after the product valve for monitoring the pressure, flow, and analyte concentrations in the system, and a waste pressure transducer (438) between the first fluid side of the forward osmosis membrane and the drain valve to the feed waste discharge reservoir. Any combination of one, two, three, zero, or all of the transducers can be used in any embodiment of the dialysate generator for increased monitoring and external control over dialysate production. Additional transducers can be added. The transducers do not require external power.

Figure 5:
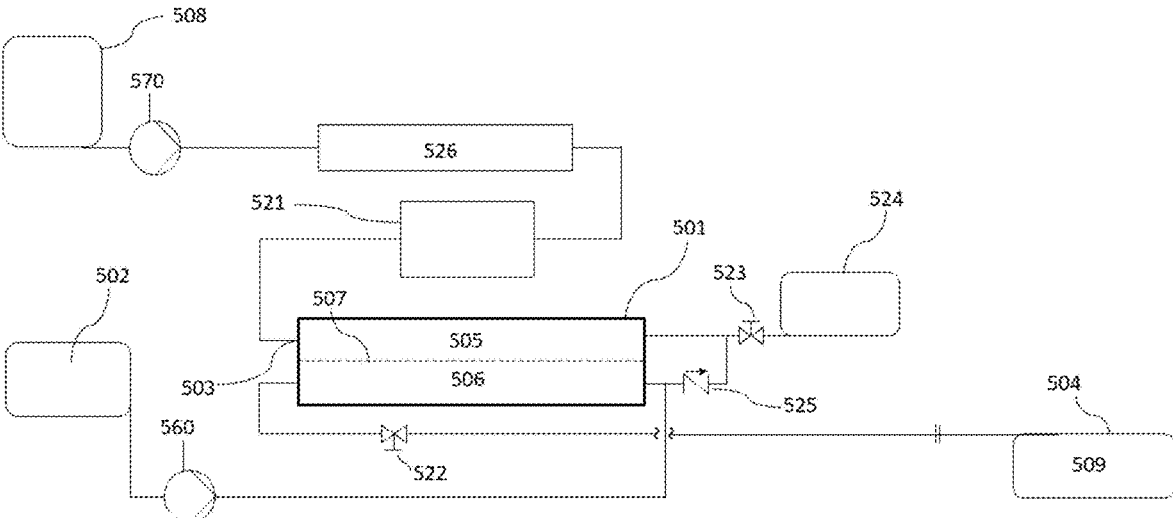
FIG. 5: Schematic of the portable dialysate generator with optional pump for injection concentrate, and optional pump for feed water.

FIG. 5. shows components and their connections for a portable dialysate generator having a forward osmosis membrane module (501); a concentrated aqueous salt solution reservoir (502); a non-sterile water feedstock inlet (503); and a collection reservoir (504). The forward osmosis membrane module has a first fluid side (505) and a second fluid side (506), the first fluid side and the second fluid side being separated by an osmosis membrane (507). Produced dialysate (509) is moved from the second fluid side to the collection reservoir (504), optionally with this flow controlled by a product valve (522). The device in FIG. 5 is man-portable: it is less than 50 pounds, preferably at most 31 pounds. Also, the portable dialysate generator may have a non-sterile water feedstock (508), which may be a stagnant reservoir mounted above the forward osmosis membrane module, operably allowing gravity-feeding of fluid from the non-sterile water feedstock reservoir into the forward osmosis membrane module. The non-sterile water feedstock may also be natural flowing water, tap water, natural still water, and other water sources in nature or provided through plumbing or water storage containers. To control or induce the flow of non-sterile water into the system, FIG. 5 includes an optional feed pump (570), which may be manual or automated. This pump may be battery-powered and removes the difficulties of lifting a feed water reservoir to a height for inducing gravity flow into the dialysate generator. The optional pump on the feed side does not generate fluid pressure to drive flow across the osmosis membrane. The optional pump generates a fluid pressure of no greater than 5 psi.

There is a prefilter (521) preceding the forward osmosis membrane for further filtration of the non-sterile feedstock water, and a carbon column (526) preceding the prefilter. Optionally, there is a drain valve (523) to control the flow of the feed water through the forward osmosis membrane module, and the drain valve may be optionally connected to a feed waste discharge reservoir (524). There is a recycling valve (525) that re-routes fluid from the sterile, second fluid side, to the feed, first fluid side, when there is pressure buildup. The portable dialysate generator in FIG. 5 has an injection concentrate pump (560), which may be manual or automated, for controlling the flow of injection concentrate to the second fluid side of the forward osmosis membrane. As shown in FIG. 5, the collection reservoir is fillable by sterile dialysate produced on the second fluid side of the forward osmosis membrane module, and there is no electric-powered pump to move a fluid from the forward osmosis membrane module into the sterile dialysate collection reservoir.

Figure 6:
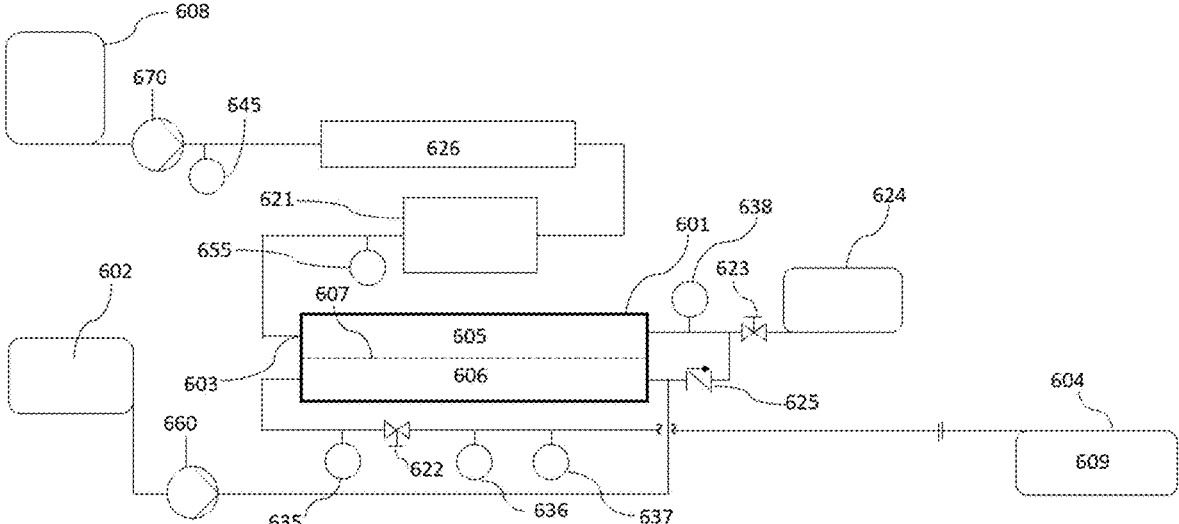
FIG. 6: Schematic of the portable dialysate generator with optional pump for injection concentrate, optional pump for feed water, and optional transmitters.

FIG. 6 shows the same components and connections for a portable dialysate generator as FIG. 5, but with additional optional transducers for externally monitoring the performance of the system. The portable dialysate generator has a forward osmosis membrane module (601); a concentrated aqueous salt solution reservoir (602); a non-sterile water feedstock inlet (603); and a collection reservoir (604). The forward osmosis membrane module has a first fluid side (605) and a second fluid side (606), the first fluid side and the second fluid side being separated by an osmosis membrane (607). Produced dialysate (609) is moved from the second fluid side to the collection reservoir (604), optionally with this flow controlled by a product valve (622). There is a prefilter (621) and a carbon column (626) preceding the forward osmosis membrane for further filtration of the non-sterile feedstock water, a drain valve (623) to control the flow of the feed water through the forward osmosis membrane module connected to a feed waste discharge reservoir (624), and a recycling valve (625) that re-routes fluid from the sterile, second fluid side, to the feed, first fluid side, when there is pressure buildup. Also, the portable dialysate generator may have a non-sterile water feedstock (608), which may be a stagnant reservoir mounted above the forward osmosis membrane module, operably allowing gravity-feeding of fluid from the non-sterile water feedstock reservoir into the forward osmosis membrane module. The non-sterile water feedstock may also be natural flowing water, tap water, natural still water, and other water sources in nature or provided through plumbing or water storage containers.

To control or induce the flow of non-sterile water into the system, FIG. 6 includes an optional feed pump (670), which may be manual or automated. This pump may be battery-powered and removes the difficulties of lifting a feed water reservoir to a height for inducing gravity flow into the dialysate generator. The pump does not pump liquid across the forward osmosis membrane. The portable dialysate generator in FIG. 6 also has an injection concentrate pump (660), which may be manual or automated, for controlling the flow of injection concentrate to the second fluid side of the forward osmosis membrane. FIG. 6 shows additional optional transducers, a product pressure transducer (635) before the product valve, a product flow transducer (636) and a product analyte transducer (637) after the product valve for monitoring the pressure, flow, and analyte concentration in the system, and a waste pressure transducer (638) between the first fluid side of the forward osmosis membrane and the drain valve to the feed waste discharge reservoir. Also, an optional feedwater temperature transducer (645) is immediately after the feed pump, and an optional sterilized feedwater flow transducer (655) is immediately after the prefilter, before the connection to the forward osmosis membrane. These optional transducers may be used in any combination of one, more than one, all, or less than all transducers in any embodiment of the portable dialysate generator for enhanced monitoring of the system. Additional transducers can be added.

Figure 7:
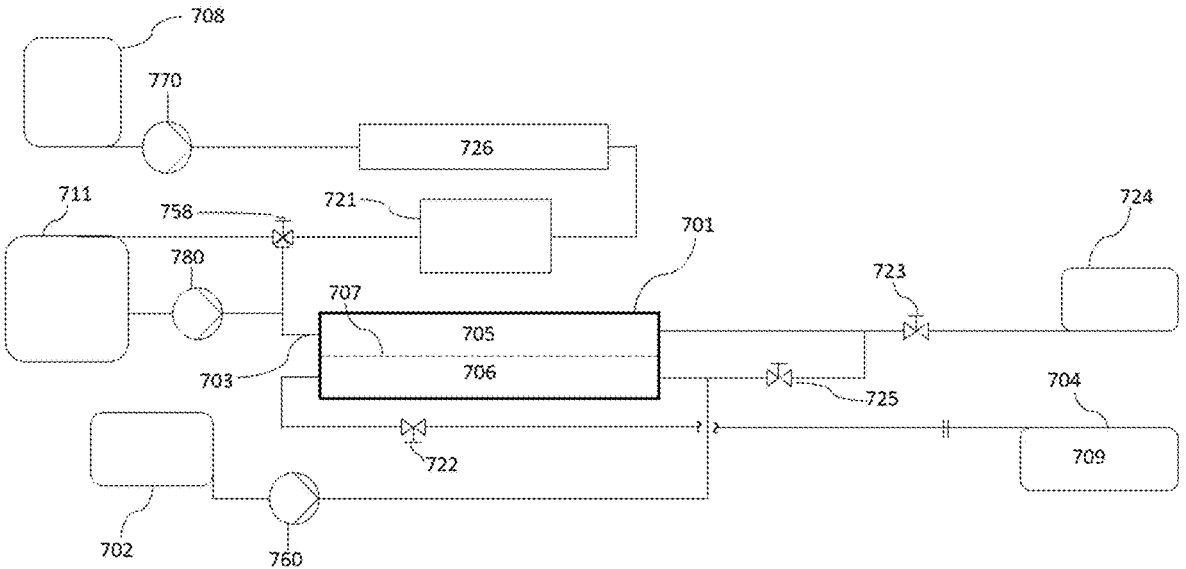
FIG. 7: Schematic of the portable dialysate generator with optional pump for injection concentrate, optional pump for feed water, and optional backflush and sterilization reservoir with optional pump.

FIG. 7 shows components and their connections for a portable dialysate generator having a forward osmosis membrane module (701); a concentrated aqueous salt solution reservoir (702); a non-sterile water feedstock inlet (703); and a collection reservoir (704). The forward osmosis membrane module has a first fluid side (705) and a second fluid side (706), the first fluid side and the second fluid side being separated by an osmosis membrane (707). Produced dialysate (709) is moved from the second fluid side to the collection reservoir (704), optionally with this flow controlled by a product valve (722). There is no power used to generate fluid pressure to drive flow across the forward osmosis membrane. Optional low-pressure pumps on the feed side (inlet side, entering the first fluid side) may be used for moving feed water but they do not generate greater than 5 psi of fluid pressure. The device in FIG. 7 is man-portable:

it is less than 50 pounds, preferably less than 31 pounds. Also, the portable dialysate generator may have a non-sterile water feedstock (708), which may be a stagnant reservoir mounted above the forward osmosis membrane module, operably allowing gravity-feeding of fluid from the non-sterile water feedstock reservoir into the forward osmosis membrane module. The non-sterile water feedstock may also be natural flowing water, tap water, natural still water, and other water sources in nature or provided through plumbing or water storage containers. To control or induce the flow of non-sterile water into the system, FIG. 7 includes an optional feed pump (770), which may be manual or automated. This pump may be battery-powered and removes the difficulties of lifting a feed water reservoir to a height for inducing gravity flow into the dialysate generator. The pump does not pump liquid across the forward osmosis membrane.

There is a prefilter (721) preceding the forward osmosis membrane for further filtration of the non-sterile feedstock water, and a carbon column (726) preceding the prefilter. Optionally, there is a drain valve (723) to control the flow of the feed water through the forward osmosis membrane module, and the drain valve may be optionally connected to a feed waste discharge reservoir (724). There is a recycling valve (725) that re-routes fluid from the sterile, second fluid side, to the feed, first fluid side, when there is pressure buildup. The portable dialysate generator in FIG. 7 has an injection concentrate pump (760), which may be manual or automated, for controlling the flow of injection concentrate to the second fluid side of the forward osmosis membrane. As shown in FIG. 7, the collection reservoir is fillable by sterile dialysate produced on the second fluid side of the forward osmosis membrane module, and there is no electric-powered pump to move a fluid from the forward osmosis membrane module into the sterile dialysate collection reservoir.

FIG. 7 shows an optional backflush and sterilization reservoir (711) connected before the forward osmosis membrane, but after any additional filtration components. The backflush and sterilization reservoir is connected via a sterile backflush valve (758), which allows excess filtered feed water to enter the reservoir. Liquid from the backflush and sterilization reservoir is fed back into the dialysate system, directed toward the forward osmosis membrane, by a sterilization pump (780) which may be manual or automated. The sterilization pump does not force liquid into or across the forward osmosis membrane.

Figure 8:
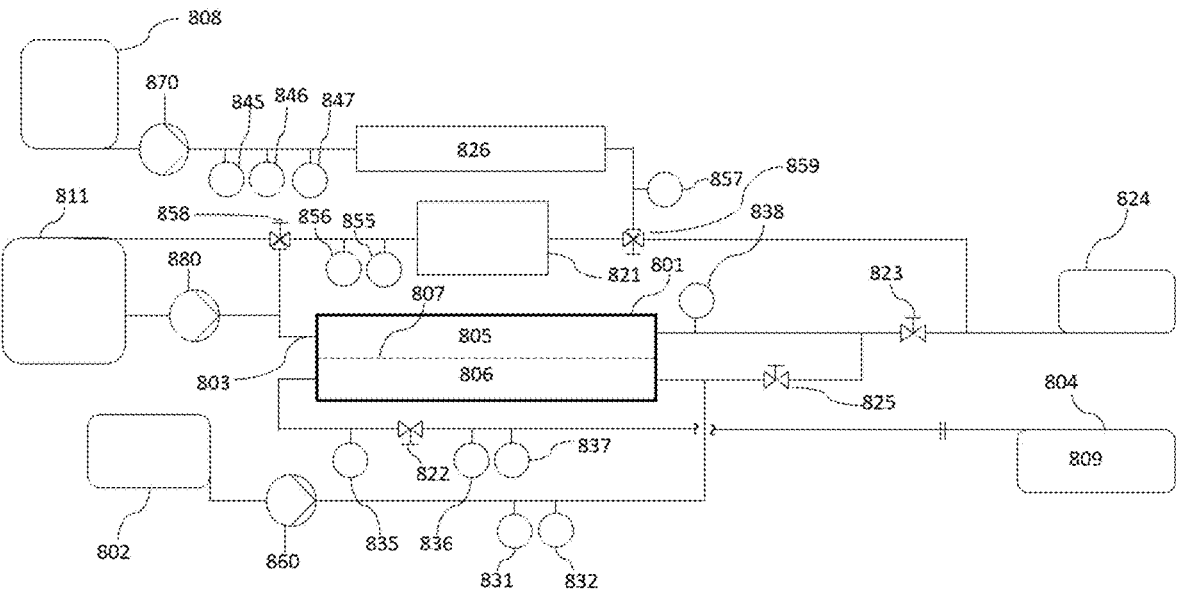
FIG. 8: Schematic of the portable dialysate generator with optional pump for injection concentrate, optional pump for feed water, optional backflush and sterilization reservoir with optional pump, and optional transmitters.

FIG. 8 shows the same components and connections for a portable dialysate generator as FIG. 7, but with additional optional transducers for externally monitoring the performance of the system. The portable dialysate generator has a forward osmosis membrane module (801); a concentrated aqueous salt solution reservoir (802); a non-sterile water feedstock inlet (803); and a collection reservoir (804). The forward osmosis membrane module has a first fluid side (805) and a second fluid side (806), the first fluid side and the second fluid side being separated by an osmosis membrane (807). Produced dialysate (809) is moved from the second fluid side to the collection reservoir (804), optionally with this flow controlled by a product valve (822). There is a prefilter (821) and a carbon column (826) preceding the forward osmosis membrane for further filtration of the non-sterile feedstock water, a drain valve (823) to control the flow of the feed water through the forward osmosis membrane module connected to a feed waste discharge reservoir (824), and a recycling valve (825) that re-routes fluid from the sterile, second fluid side, to the feed, first fluid side, when there is pressure buildup. The portable dialysate generator may have a non-sterile water feedstock (808).

FIG. 8 shows a feed pump (870), which may be manual or automated, for controlling or inducing flow into the dialysate generator. Sterilized feed water may be directed via a sterile reservoir valve (858) from a backflush and sterilization reservoir (811). Liquid from this reservoir may be pumped into the forward osmosis membrane, directed toward the forward osmosis membrane, by a sterilization pump (880), which may be manual or automated, or back through the prefilter and directed to the discharge reservoir with the sterile backflush valve (859). FIG. 8 also shows an injection concentrate pump (860) for controlling the flow of injection concentrate to the second fluid side of the forward osmosis membrane.

FIG. 8 comprises 12 additional optional transducers throughout the portable dialysate generator. Each of these transducers is individually optional, and any combination of one, more than one, 1-12, less than all, none, or all transducers may be used in any embodiment of the portable dialysate generator described herein. FIG. 8 shows a product pressure transducer (835) before the product valve, a product flow transducer (836) and a product analyte transducer (837) after the product valve for monitoring the pressure, flow, and analyte concentration in the system, and a waste pressure transducer (838) between the first fluid side of the forward osmosis membrane and the drain valve to the feed waste discharge reservoir. An optional feedwater temperature transducer (845), a feedwater pressure transducer (846), and a feedwater analyte transducer (847) are immediately after the feed pump, and an optional second sterilized feedwater flow transducer (855) and a sterilized feedwater pressure transducer (856) are immediately after the prefilter, before the sterile backflush valve. A mid-filtration pressure transducer (857) is between the carbon column and the prefilter. An injection concentrate flow transducer (831) and an injection concentrate pressure transducer (832) are located between the injection concentrate pump and the second fluid side of the forward osmosis membrane. Additional transducers can be added.

Figure 9:
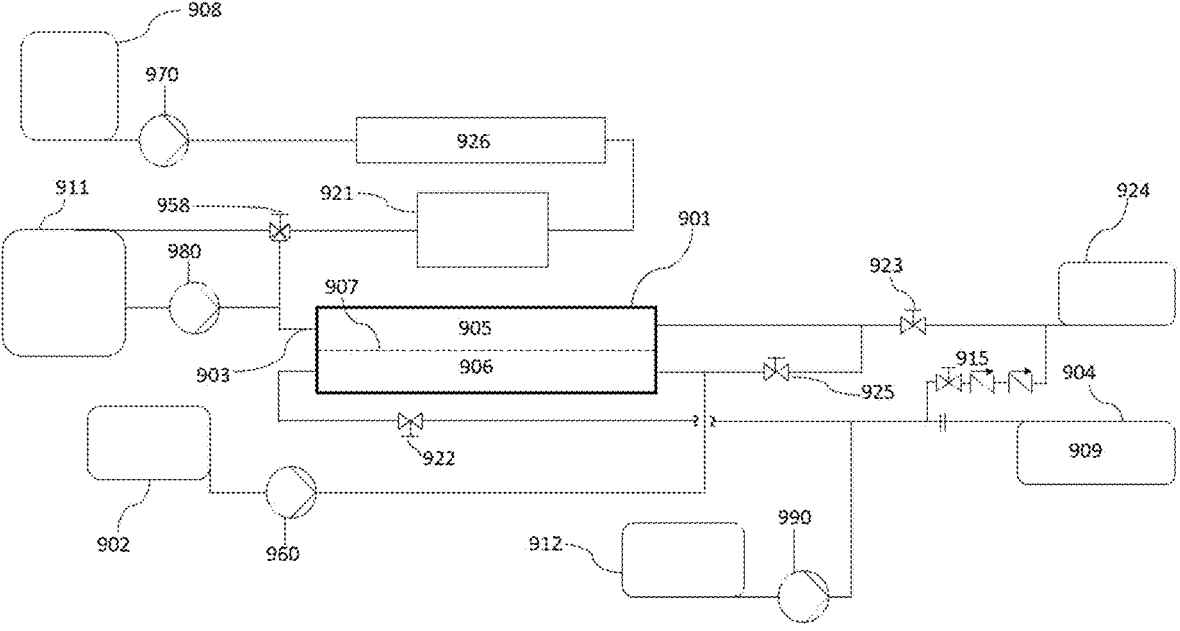
FIG. 9: Schematic of the portable dialysate generator with optional pump for injection concentrate, optional pump for feed water, optional pump for backflush and sterilization, and optional acid reservoir with optional pump.

FIG. 9 shows another embodiment of the portable dialysate generator, with components and their connections for a portable dialysate generator having a forward osmosis membrane module (901); a concentrated aqueous salt solution reservoir (902); a non-sterile water feedstock inlet (903); and a collection reservoir (904). The forward osmosis membrane module has a first fluid side (905) and a second fluid side (906), the first fluid side and the second fluid side being separated by an osmosis membrane (907). Produced dialysate (909) is moved from the second fluid side to the collection reservoir (904), optionally with this flow controlled by a product valve (922). There is a prefilter (921) and a carbon column (926) preceding the forward osmosis membrane for further filtration of the non-sterile feedstock water, a drain valve (923) to control the flow of the feed water through the forward osmosis membrane module connected to a feed waste discharge reservoir (924), and a recycling valve (925) that re-routes fluid from the sterile, second fluid side, to the feed, first fluid side, when there is pressure buildup. FIG. 9 also shows an optional bypass valve (915). The portable dialysate generator may have a non-sterile water feedstock (908). There is no power used to generate fluid pressure to drive flow across the forward osmosis membrane. Optionally, there are low-pressure pumps on the feed side of the device, but the pumps generate no greater than 5 psi of fluid pressure at the forward osmosis membrane surface.

FIG. 9 shows a feed pump (970), which may be manual or automated, for controlling or inducing flow into the dialysate generator. Sterilized feed water may be directed via a sterile reservoir valve (958) from a backflush and sterilization reservoir (911). Liquid from this reservoir may be pumped into the forward osmosis membrane, directed toward the forward osmosis membrane, by a sterilization pump (980), which may be manual or automated. FIG. 9 also shows an injection concentrate pump (960) for controlling the flow of injection concentrate to the second fluid side of the forward osmosis membrane. FIG. 9 further comprises an acid reservoir (912) for pH adjustment of the produced dialysate solution before it enters the collection reservoir. An acid pump (990), which may be manual or automated, controls the flow of acid into the produced dialysate solution.

Figure 10:
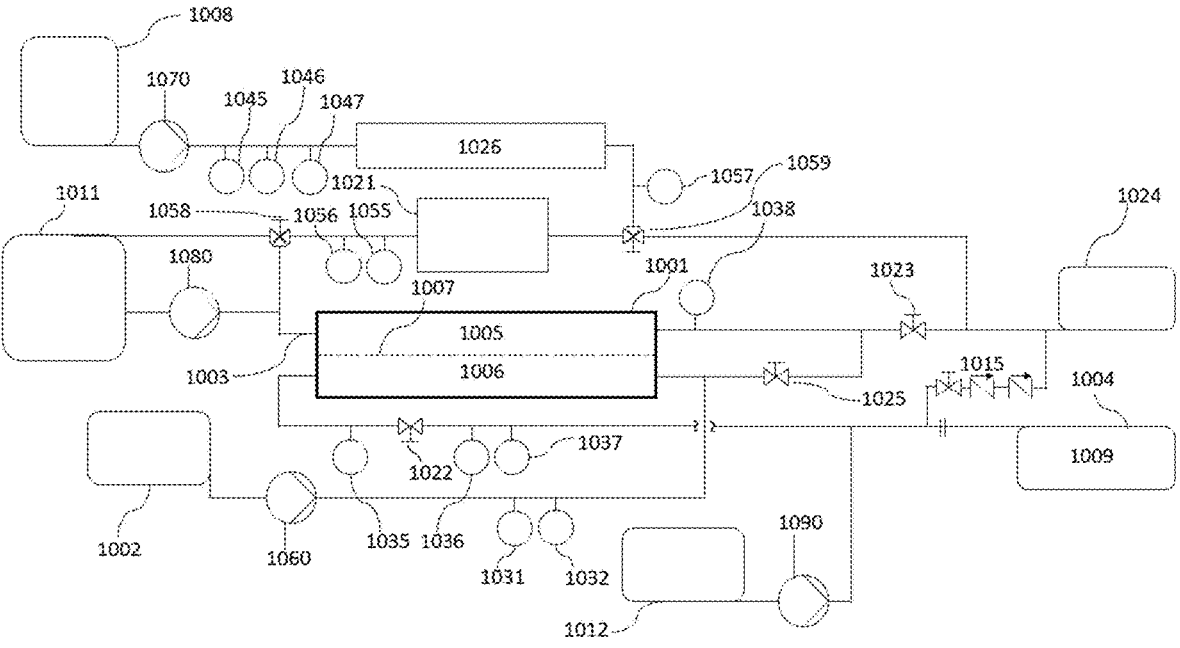
FIG. 10: Schematic of the portable dialysate generator with optional features.

FIG. 10 shows the same components and connections for a portable dialysate generator as FIG. 9, but with additional optional transducers for externally monitoring the performance of the system. FIG. 10 shows another embodiment of the portable dialysate generator, with components and their connections for a portable dialysate generator having a forward osmosis membrane module (1001); a concentrated aqueous salt solution reservoir (1002); a non-sterile water feedstock inlet (1003); and a collection reservoir (1004). The forward osmosis membrane module has a first fluid side (1005) and a second fluid side (1006), the first fluid side and the second fluid side being separated by an osmosis membrane (1007). Produced dialysate (1009) is moved from the second fluid side to the collection reservoir (1004), optionally with this flow controlled by a product valve (1022). There is a prefilter (1021) and a carbon column (1026) preceding the forward osmosis membrane for further filtration of the non-sterile feedstock water, a drain valve (1023) to control the flow of the feed water through the forward osmosis membrane module connected to a feed waste discharge reservoir (1024), and a recycling valve (1025) that re-routes fluid from the sterile, second fluid side, to the feed, first fluid side, when there is pressure buildup. FIG. 10 also shows an optional final bypass (1015). The portable dialysate generator may have a non-sterile water feedstock (1008).

FIG. 10 shows a feed pump (1070), which may be manual or automated, for controlling or inducing flow into the dialysate generator. Sterilized feed water may be directed via a sterile reservoir valve (1058) from a backflush and sterilization reservoir (1011). Liquid from this reservoir may be pumped into the forward osmosis membrane, directed toward the forward osmosis membrane, by a sterilization pump (1080), which may be manual or automated, or back through the prefilter and directed to the discharge reservoir with the sterile backflush valve (1059). FIG. 10 also shows an injection concentrate pump (1060) for controlling the flow of injection concentrate to the second fluid side of the forward osmosis membrane. FIG. 10 further comprises an acid reservoir (1012) containing an additive for pH adjustment of the produced dialysate solution before it enters the collection reservoir. An acid pump (1090), which may be manual or automated, controls the flow of acid into the produced dialysate solution.

FIG. 10 comprises 12 additional optional transducers throughout the portable dialysate generator. Each of these transducers is individually optional, and any combination of one, more than one, 1-12, less than all, none, or all transducers may be used in any embodiment of the portable dialysate generator described herein. FIG. 10 shows a product pressure transducer (1035) before the product valve, a product flow transducer (1036) and a product analyte transducer (1037) after the product valve for monitoring the pressure, flow, and analyte concentration in the system, and a waste pressure transducer (1038) between the first fluid side of the forward osmosis membrane and the drain valve to the feed waste discharge reservoir. An optional feedwater temperature transducer (1045), a feedwater pressure transducer (1046), and a feedwater analyte transducer (1047) are immediately after the feed pump, and an optional second sterilized feedwater flow transducer (1055) and a sterilized feedwater pressure transducer (1056) are immediately after the prefilter, before the sterile backflush valve. A mid-filtration pressure transducer (1057) is between the carbon column and the prefilter. An injection concentrate flow transducer (1031) and an injection concentrate pressure transducer (1032) are located between the injection concentrate pump and the second fluid side of the forward osmosis membrane. Additional transducers can be added.

Figure 25:
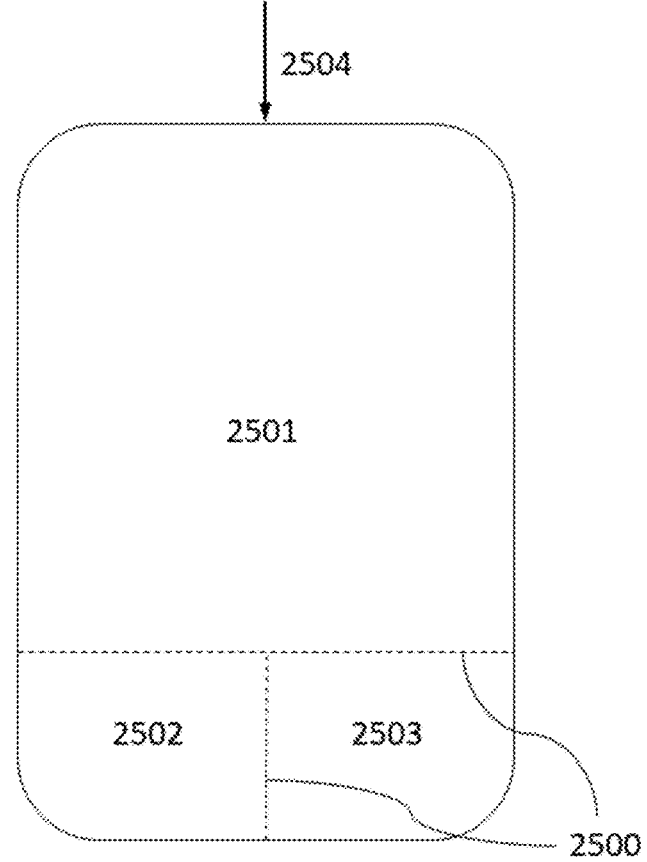
FIG. 25: Optional fillable product collection bad with additional compartments.

In some embodiments, the collection reservoir is a flexible and fillable bag like the one shown in FIG. 25. Produced dialysate (2504) flows into a first compartment (2501) which holds 1 L or 5 L in some embodiments. A second compartment (2502) contains bicarbonate and a third compartment (2503) contains an acid for pH adjustment to the desired range for dialysate, with both compartments separated from the first compartment and each other with a frangible seal (2500).

Figure 11:
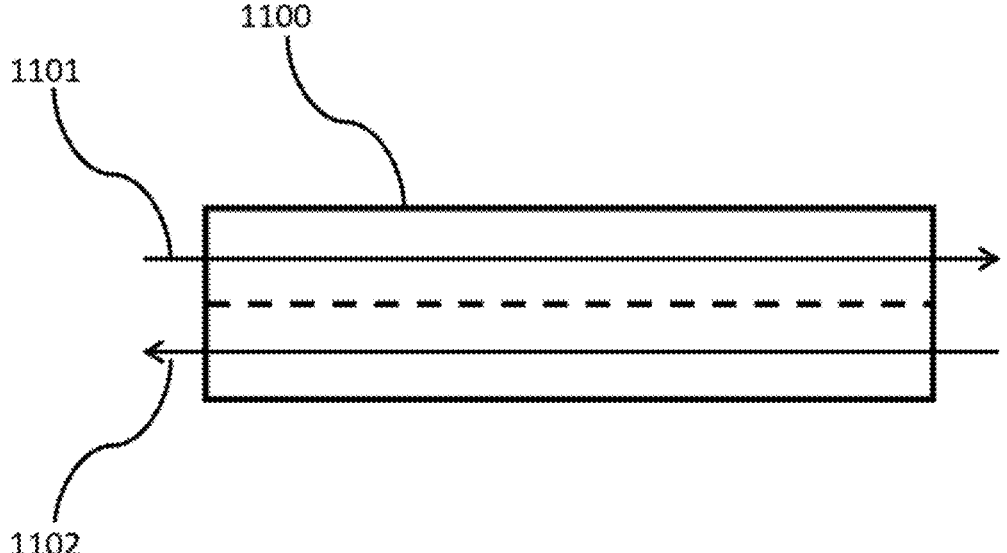
FIG. 11: Forward osmosis module.

FIG. 11 shows a forward osmosis membrane module (1100), and non-sterile water inlet (1101) and a counter current configuration (1102).

Figure 12:
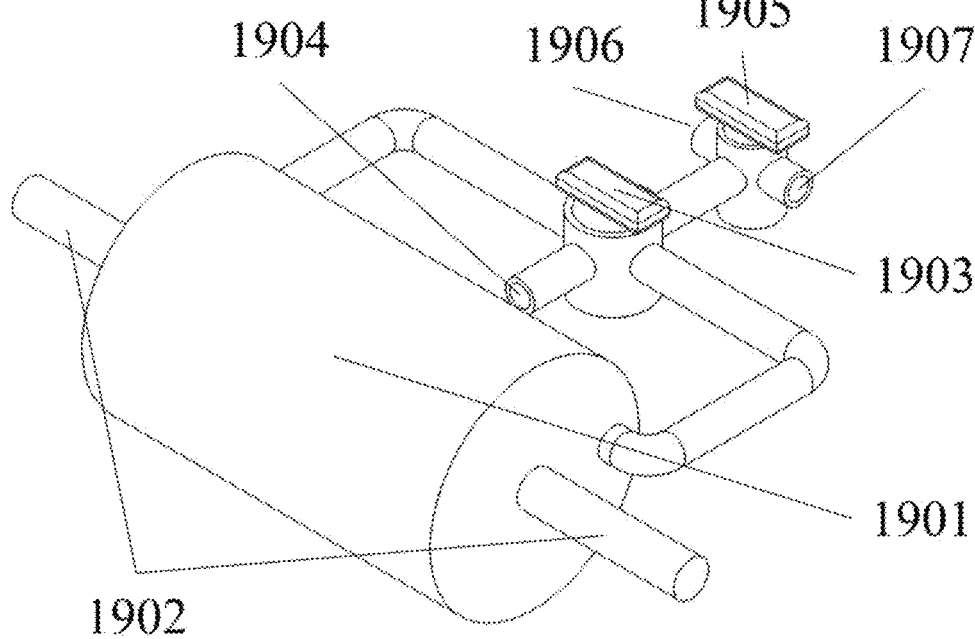
FIG. 12: External view of a two-stroke fillable piston reservoir.

Further optional description of the two stroke-piston reservoir is shown in FIG. 12. A piston housing (1901) contains a double rod piston (1902), though in an alternative embodiment a regular piston can be used; a 4-way valve (1903) is in fluid communication with each side of the two stroke piston and also in fluid communication with a dialysate fluid exit (1904); the inlet to the 4-way valve is in fluid communication with a 3-way T valve (1905); and the 3-way T valve is in fluid communication with a dialysate fluid inlet (1906) and a sterile air inlet (1907). Alternate designs may be used to operate the same function.

Figure 13:
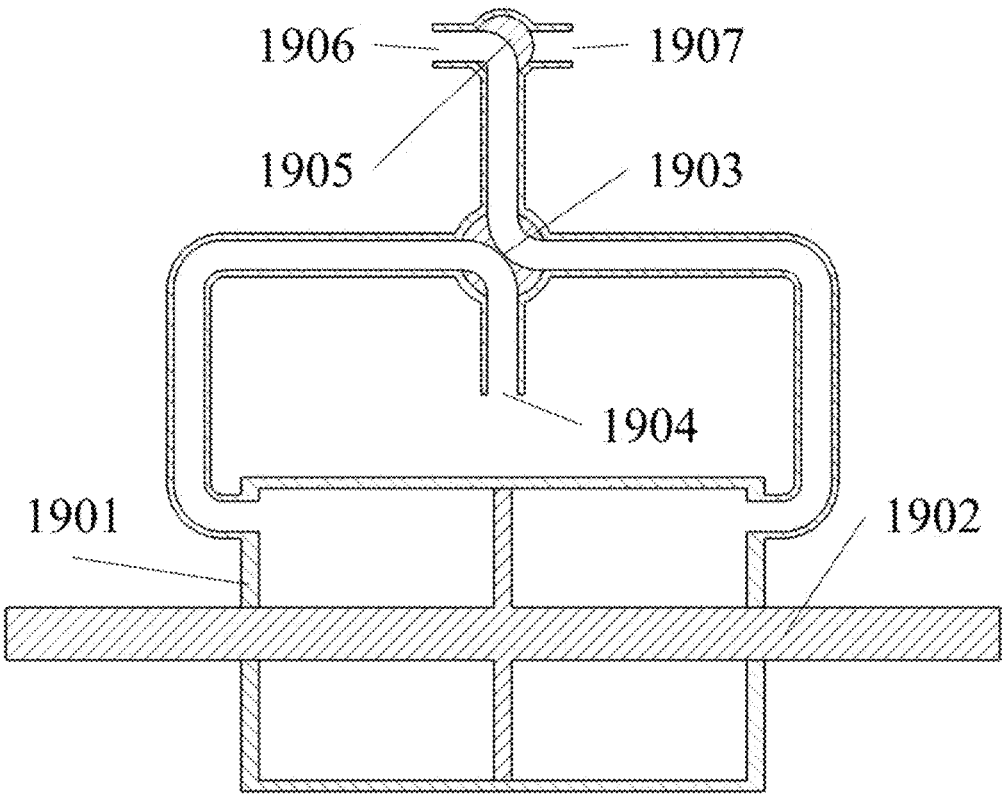
FIG. 13: Cross section of a two-stroke fillable piston reservoir.

FIG. 13 shows the cross section of the device in FIG. 12. Also, the piston is in the center position.

Figure 14:
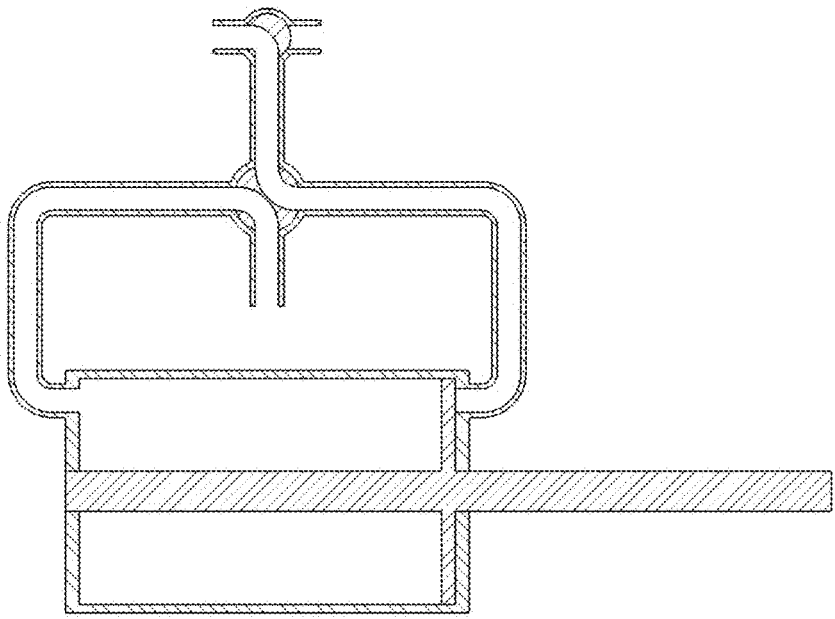
FIG. 14: Cross section of a two-stroke fillable piston reservoir with the 4-way valve in position Valve-1 and the piston in position Piston-1 (right).
Figure 15:
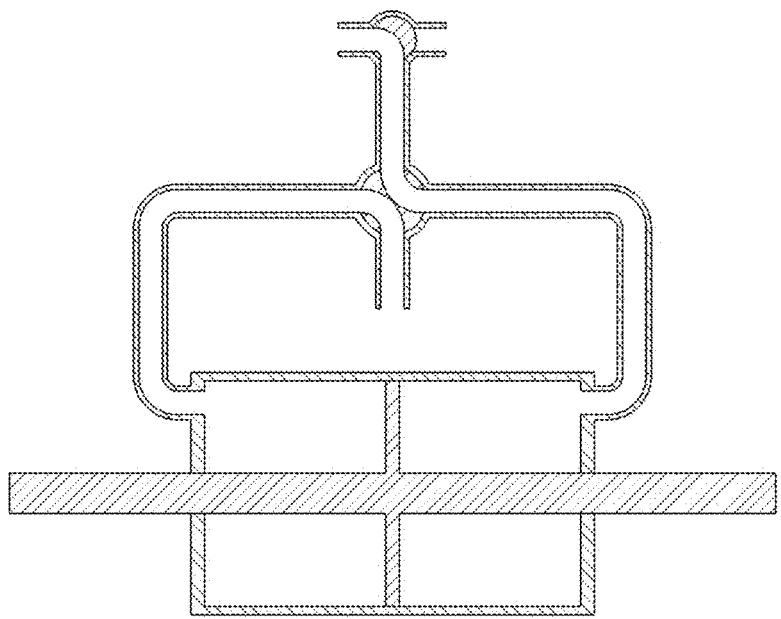
FIG. 15: Cross section of a two-stroke fillable piston reservoir with the 4-way valve in position Valve-1 and the piston in position Piston-2 (middle).
Figure 16:
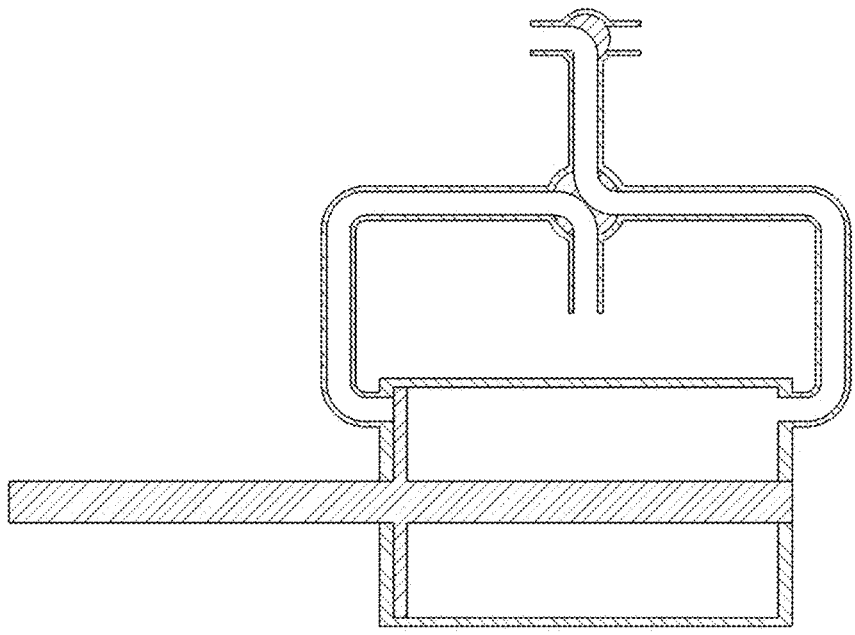
FIG. 16: Cross section of a two-stroke fillable piston reservoir with the 4-way valve in position Valve-1 and the piston in position Piston-3 (left).
Figure 17:
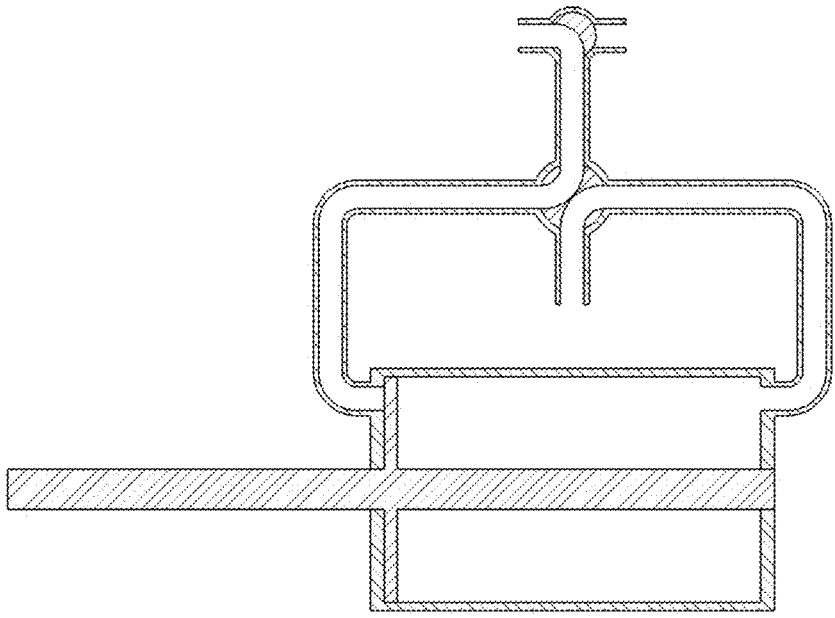
FIG. 17: Cross section of a two-stroke fillable piston reservoir with the 4-way valve in position Valve-2 and the piston in position Piston-3 (left).
Figure 18:
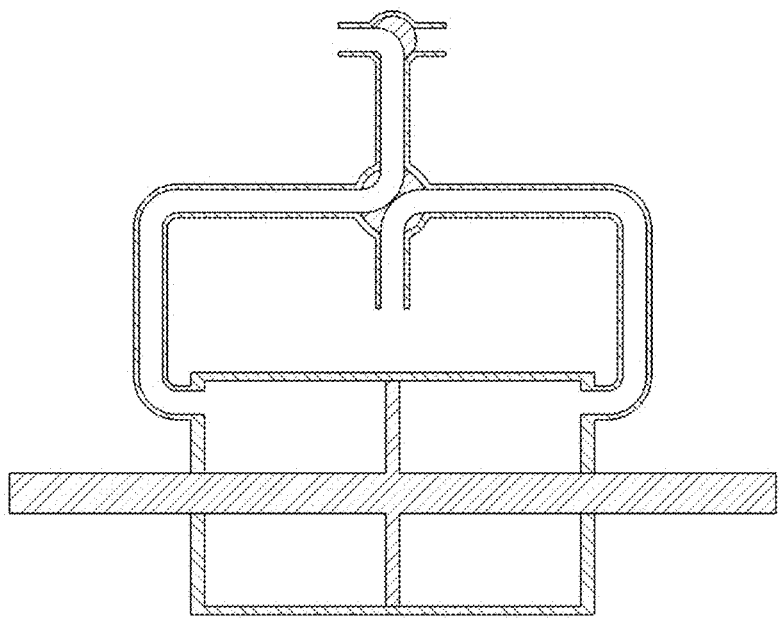
FIG. 18: Cross section of a two-stroke fillable piston reservoir with the 4-way valve in position Valve-2 and the piston in position Piston-2 (middle).
Figure 19:
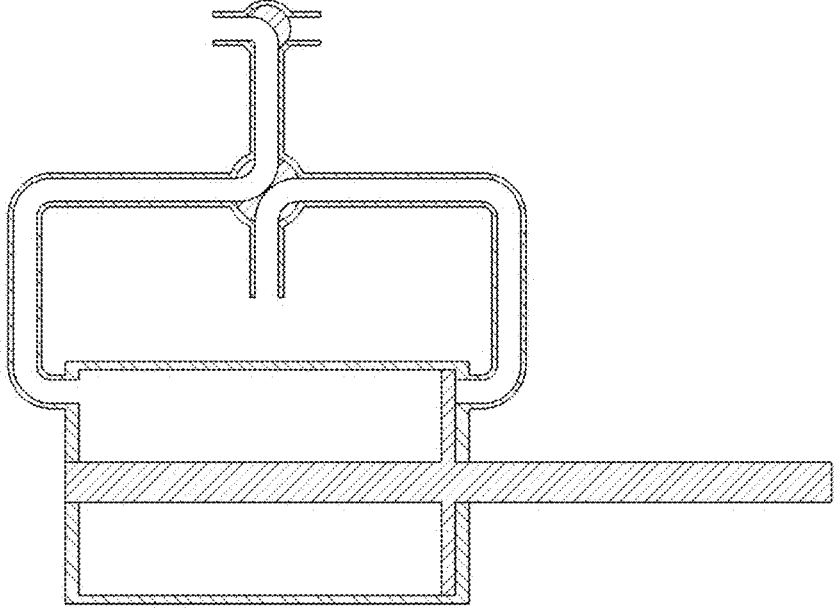
FIG. 19: Cross section of a two-stroke fillable piston reservoir with the 4-way valve in position Valve-2 and the piston in position Piston-1 (right).
Figure 20:
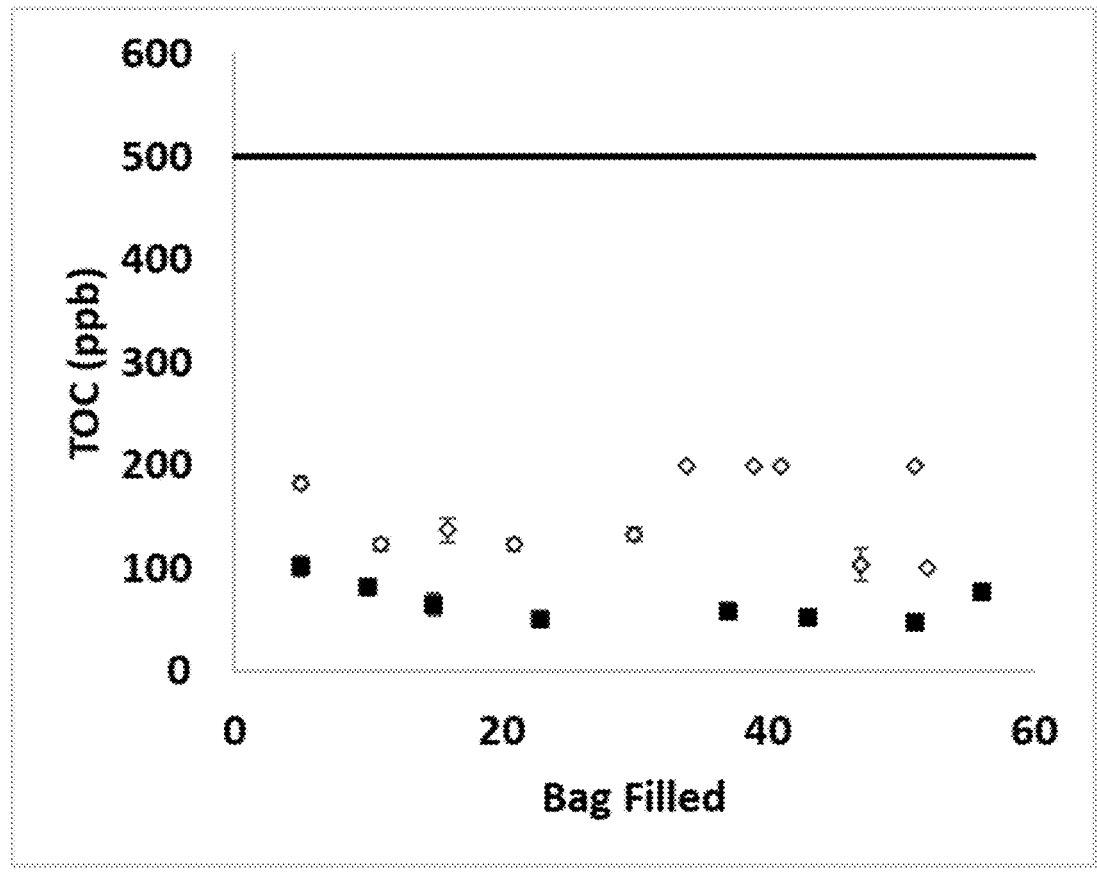
FIG. 20: Measured TOC for dialysate produced by the generator.

FIGS. 14-19 show the sequence of 4-way valve positions and piston positions for filling the first side and then simultaneously filling the second side and dispensing the first side. FIG. 14 shows a cross section of a two-stroke fillable piston reservoir with the 4-way valve in position Valve-1 and the piston in position Piston-1 (right). FIG. 15 shows a two-stroke fillable piston reservoir with the 4-way valve in position Valve-1 and the piston in position Piston-2 (middle). FIG. 16 shows a two-stroke fillable piston reservoir with the 4-way valve in position Valve-1 and the piston in position Piston-3 (left). FIG. 17 shows a two-stroke fillable piston reservoir with the 4-way valve in position Valve-2 and the piston in position Piston-3 (left). FIG. 18 shows a two-stroke fillable piston reservoir with the 4-way valve in position Valve-2 and the piston in position Piston-2 (middle). FIG. 19 shows a two-stroke fillable piston reservoir with the 4-way valve in position Valve-2 and the piston in position Piston-1 (right).

The components are as follows: the three-way T valve (1903) the four-way L-flow diverter valve (1905), the piston housing (1901), the double rod piston (1902), the dialysate fluid inlet (1906), the sterile air inlet (1907), and the dialysate fluid exit (1904). The dialysate fluid exit (1904) may attach to a collection vessel, such as a flexible 1 L or 5 L bag.

The system functions are carried out in cycles where the piston and valve positions change. There are two types of cycle the generator can run, the fill cycle and the purge cycle. In the fill cycle dialysate fluid enters from the inlet and fills into one side of the piston housing, actuating the piston. Fluid on the other side of the piston is forced out of the housing through the system outlet. Filling can occur in either direction with proper orientation of the four-way diverter valve. This enables repeated production of a set volume of dialysate fluid, since the volume of the piston housing is constant. A trigger mechanism may be coupled to the rods on the piston to automate switching of the diverter valve. The piston rods maintain sterility outside of the housing through use of an intermediary sterilant reservoir/wiper and boot system. A fill cycle is illustrated in drawings 14 through 16. The cycle starts arbitrarily with the piston on the right-hand side. Fluid begins to enter the system due to induction of osmotic pressure in the Aquaporin module. The piston slides from right to left, once it hits the left-hand wall a pressure spike occurs which causes an auto shutoff valve to actuate further back in the flow path (not pictured here), ceasing flow. The diverter valve is switched, the auto shutoff valve reset, and flow initiated again with a saline injection into the clean side of the Aquaporin module to drive the piston back and repeat the cycle. Dialysate which filled the piston in the previous step is pushed out of the system outlet into a collection vessel. The piston displaces the same volume of fluid each cycle, so production levels are consistent from run to run.

After producing the desired quantity of dialysate, the system can be emptied through the purge cycle. The system outlet is directed towards a disposal basin and the T valve turned to allow flow from the sterile air inlet. A size exclusion membrane (not pictured) allows atmosphere to enter the system without introducing microbes. The piston moves with the diverter valve in the same manner as when filling. However, the force driving the piston is not osmotic pressure. Instead, piston actuation is carried out manually by applying force to the appropriate piston rod. This can be accomplished with a mechanical advantage provided via lever or screw. This may also be automated. A full purge cycle is shown in drawings 17 to 19. Alternatively to the process shown in FIGS. 14-19, air can be pumped (manually or automated) in through the sterile air inlet and used to move the piston.

The dialysate generator may use a multistage filtration process to produce sterile dialysate. Feed water (potable or non-potable) first flows through a carbon column, where dissolved organics are stripped from the water. This source water may be hung above the dialysate generator, to allow for a gravity fed mechanism. The source water may alternatively be pumped into the system by a manual or automated pump, to allow use of feedwater sources such as tap water, natural water (rivers, lakes, ponds, and the like), and stored water in larger containers that cannot be lifted above the dialysate generator for gravity feeding. A feed water pump used in any embodiment would not pump water across the forward osmosis membrane or into the collection reservoir, but only control the flow of feed water into the system to mimic a gravity flow. The carbon column is preferably sized to produce 50 L of dialysate for every column used. This carbon removal is optional in the system, as the forward osmosis membrane is also an extremely effective barrier to organic contaminants. There is no defined standard for acceptable TOC limits in dialysis fluid, as the controls around system design (i.e. carbon and RO based systems) are sufficient for organic carbon removal. The present invention provides effective TOC removal, and meets the requirements for water for hemodialysis system design by including a carbon-based adsorption system, and an RO equivalent membrane (FO in this system).

From the carbon column water flows into a hollow fiber membrane (HFM) microfilter, which removes particulates and biological contaminants. Alternatively, the forward osmosis membrane module may be any of the variations described in the definition for "osmosis membrane". The filter preferably has a 0.2 μm pore size, the accepted standard for a sterilizing filter. The primary purpose of this filter is particulate removal prior to the forward osmosis (FO) filtration. Large particulates can damage or clog the FO membrane, reducing overall system efficiency. However, this filter also serves as an initial, redundant bio-burden reduction filter. Adding this redundancy keeps any contamination further away (in the flow path) from the sterile portion of the system, and helps improve system efficiency by sending sterile, TOC free water to the FO membrane.

The final filter is a highly water-selective forward osmosis (FO) membrane. In addition to serving as the final barrier to biologic contamination and TOC, which are dealt with up-stream, the FO membrane de-ionizes the water and rejects any additional contaminants (such as heavy metals and other inorganic contaminants). The result is that only pure, sterile water is able to cross the FO membrane. The filter is a hollow fiber tube bundle (although other membrane designs could be used), in which water is fed into the tubes (lumen side) and is filtered radially out of the tubes to the shell side (which is where dialysate is injected and flows). There are 4 entry/exit points on the membrane module in the device: two on the feed side (lumen side entry/outlet) and two on the sterile side (shell side entry/exit). This allows the feed water entering the FO module to flow out in two possible paths. It can either enter, and exit, while remaining on the lumen side, or it can enter on the lumen and flow radially across the fibers to the shell side. In a preferred embodiment the first path (remaining on the lumen side) is used to flush the system before each run. This pathway leads to an automatic discharge or drain valve, which can be turned to allow flow (by gravity or by pump) from the source water through the pre-filtration train (carbon and microfilter) and through the lumen side of the FO module to a discharge. This path is used prior to each production run to clean out previously filtered water, which will become concentrated in any ions or contaminants not removed upstream. This concentration of dirty water occurs as clean, pure water is pulled across the FO membrane fibers, leaving the contaminants behind. As more and more water is filtered and removed from the batch of feed water, the concentration of contaminants increases. This has the effect of decreasing the osmotic pressure differential, and therefore decreasing the driving force. It is important to clear this liquid out before the start of each run to maximize the osmotic pressure differential, and maximize the system driving force.

FO is a water transport process in which water (and essentially only water) moves from low solute (electrolytes in the case of the dialysate generator) concentrations to high solute concentrations across a semi-permeable membrane without any added energy (e.g. a pump). This process is a result of the concentration difference across the membrane. The driving force for this process is osmotic pressure, which is defined as the amount of pressure required to prevent flow across the membrane (and consequently the pressure equivalent force driving flow). Osmotic pressure differential is calculated as $\pi=RT\Delta C$, where $\pi$ is the osmotic pressure, R is the gas constant, T is temperature, and $\Delta C$ is the concentration difference across the membrane.

The device of the present invention leverages FO by using a small injection (40 mL injection solution per 1.0 L of produced dialysate) of sterile, highly concentrated dialysate to generate ~3,100 psi of initial driving force (osmotic pressure). The injection creates a large concentration gradient across the membrane, which generates the massive force to push water across the membrane. This quickly pulls water through the filtration train and across the FO membrane where it dilutes the concentrate to produce dialysate with no power, at an extremely rapid rate of 7-10 L/hr (2-3 times the required rate generally required in emergency situations). As the dialysate concentrate is diluted to the correct dialysate concentration, the osmotic pressure differential decreases in an exponential fashion (exponential due to the low volume of the injection, so 40 mL of pure water halves the osmotic pressure, then 80 mL halves it again). The system finishes with an osmotic pressure differential near that of dialysate (~100 psi). The dialysate leaving the chamber has a lower conductivity than dialysate (less than ~50 psi). Due to the change in pressure differential over the course of production, the flow rate in the system starts extremely high and slowly decreases.

The present invention teaches that operating the device in a crossflow (counter-current) orientation results in an increased production rate. This crossflow orientation is expected to maximize the unit efficiency, by maximizing osmotic pressure differential at each point along the membrane as the cleanest water meets the least concentrated draw solution, and the dirtiest water meets the most concentrated draw solution. It is expected that this orientation also maintains a higher concentration of the concentrate in the system compared to a co-current system (injection and feed are on the same side). Although not wishing to be bound by theory, when the feed and injection on the same side the concentrated injection is pushed out of the module faster, where the counter-current system acts to keep that concentrated injection in the module. In a preferred embodiment the system uses a vertically oriented module to maximize the effect of the injection being retained in the module for longer stretches of the production run. In this system, the injection enters the bottom of the module. Since salt water is heavier than relatively less saline water, the injection has a tendency to stay towards the bottom of the module, thus assisting the counter-current system in maintaining a larger osmotic driving force for longer. The produced dialysate exits from the top of the module, from the upper shell-side exit point.

In a preferred configuration, the produced dialysate is measured in precisely 1 L increments using a piston and cylinder system, which ensures each batch of dialysate has the correct ion concentration. This concentration is ensured by correct volume measurement, and careful control of the injection solution (as well as reproducibility of the system flow). The piston system uses a dual entry/exit piston design, where the produced dialysate can enter from either side of the piston. Freshly produced dialysate enters the cylinder via one of the two paths through the valve. The fluid being produced pushes the previous batches fluid into a final fill container. In the two-stroke system, and by switching the flow direction on each production batch, the dialysate from the previous run is dispensed. Using this method, the operator does not have to manually plunge the cylinder after each production batch. On the final production batch, the entire cylinder can be plunged so that it can be stored dry. The flow direction is controlled by a diverter valve, which has 4 ports. The ports line up such that the flow can come from the Dialysate Generator, through the diverter valve, and into either side of the cylinder. Similarly, the flow can exit from either side of the cylinder and pass through the diverter valve to exit the system. A teaching of the invention is that a positive displacement system is the most accurate, leading to the most consistent dialysate compositions. To reduce the production cycle time, and demands of an operator, the oscillating piston system solves this limitation. In a more automated system, using battery power in some components, the 1 L increments may be measured by a flow meter, which automatically turns the system off after a certain amount of liquid has flowed through the system. A flow cell attached to the collection reservoir may also be used. The automated embodiments of measuring the produced dialysate eliminates the need for the piston and cylinder system, though it may be used as an additional check in other embodiments.

The sterile dialysate collection reservoir is either a flexible and fillable bag or is a movable piston, wherein the sterile dialysate collection reservoir is operably connected to the forward osmosis membrane module so that excess fluid volume that can be produced in the forward osmosis membrane module can fill the sterile dialysate collection reservoir. The portable dialysate generator may, as a collection reservoir, have a two-stroke piston with a first collection reservoir side and a second collection reservoir side, and a four-way valve, wherein the four-way valve can switch the fluid communication of the forward osmosis membrane module to the first collection reservoir side or to the second collection reservoir side. The four-way valve is positioned so that the two-stroke piston moves to accommodate excess fluid volume that can be produced in the forward osmosis membrane module to fill the first collection reservoir side, while fluid contents in the second collection reservoir side are expelled into the final dialysate product collection reservoir. The final fill container may comprise a bag reservoir with a first compartment (2501) where the produced dialysate (2504) flows into and a second compartment (2502) where an additional additive is stored, either as a solid or a liquid, and an optional third compartment (2503) where an acid for pH adjustment is stored, and a frangible seal (2500) separating each compartment which can be broken to mix the compartments. It may comprise a flexible and fillable bag, of any size such as 0.5 L, 1 L, 2 L, 3 L, 4 L, 5 L, perhaps with extra space for overfill.

From the piston, the dialysate is dispensed into a final fill container (dialysate bag), which can be used to administer dialysis to patients in need. This container is connected to the system via a series of sterile, needleless connectors. This allows multiple disconnect and reconnect cycles, provided proper sterile procedure (swabbing of surfaces) is followed. The final fill container is a 5 L dialysis bag, similar to commercially available pre-made dialysis solution bags for purchase. The present invention also teaches a dual chamber dialysate bag, comprised of the filling chamber where the solution coming from the dialysate generator is stored, and a sodium bicarbonate chamber. The sodium bicarbonate chamber will contain enough powder sodium bicarbonate for 5 L of dialysate and is separated from the filling chamber by a frangible seal. To use the dialysate, the operator simply squeezes the bag until the frangible seal is broken, and then mixes the solution until the sodium bicarbonate powder has been fully dissolved.

It is a teaching of the present invention that keeping the sodium bicarbonate separate from the bulk dialysate solution is preferred. The electrolyte mix of the dialysate contains calcium chloride, and magnesium chloride. When mixed with sodium bicarbonate, these salts have the potential to form calcium carbonate and magnesium carbonate, which are solids and will precipitate out of solution. Keeping them separate until use solves several problems. First, it allows for long term storage of the produced dialysate. The precipitation reaction removes calcium, magnesium, and carbonate from the dialysate, which alters the concentration (this is not desirable). If they are kept separate until use, proper concentrations can be ensured. Second, it removes any precipitation reactions within the dialysate generator. Conversely, a dual injection system, in which an acid and electrolyte solution is injected with a sodium bicarbonate solution, was produced to generate the fully mixed dialysate on the back-end. With prolonged use, this led to precipitation build-up in the system. Shifting to a single injection of acid and electrolytes resulted in a complete elimination of this issue. Third, the system is much more weight efficient using solid sodium bicarbonate addition rather than a solution. Sodium bicarbonate has limited solubility, so a 40 mL injection was required to get enough into solution, compared to the 40 mL injection used for the remainder of the components. This effectively halves the weight efficiency of the unit, because twice the liquid volume is needed for each batch. Comparatively, only 2.7 grams of sodium bicarbonate salt are needed for each L of production, which equates to about 7% of the previous required weight (which was mostly water). Since the bulk of the lifetime weight comes from shipped consumables, and shipped liquids in particular, this is a massive improvement in the Dialysate Generators weight efficiency (saving 80 lbs. of shipped weight over the lifetime of the unit). As auxiliary benefits, the system is easier to operate, owing to the single injection vs needing two injections at the same time, and there is less likelihood of contamination. A known problem with sodium bicarbonate solutions is that they are excellent growth media for microbes. Solid sodium bicarbonate does not have the same issue. While keeping a sodium bicarbonate solution is certainly possible, using a solid is a good way to eliminate a potential source of contamination. It is preferred to use a collection vessel with three compartments: a first compartment for produced dialysate to flow into, a second compartment for bicarbonate solid or solution, and a third compartment for an acid. To prevent mixture of the components, frangible seals can be used as barriers which can be broken upon use with a patient.

Due to the osmotic pressure gradient, the pressure on the shell side of the membrane will continue to increase after the dialysate flow path is shut down or redirected due to the collection reservoir being full, or other stoppages in the flowpath after the forward osmosis module. This pressure can become extreme enough to damage the forward osmosis membrane. Damage to the membrane can include problems such as active layer lift-off, which peels away the FO membrane from its support structure, and effectively creates a hole in the membrane. This damage should be avoided to ensure the membrane remains intact and can continue to provide the necessary filtration efficiency and selectivity. To dissipate pressure, the present invention teaches a device that uses a pressure actuated relief recycle. The recycle inlet is located on the bottom entry point to the shell side of the FO module (which is where the injection also comes in). The recycle runs to the bottom outlet on the lumen side of the FO module, before the discharge valve. The line is controlled by a high cracking pressure check valve (18 psi in a nonlimiting example). Other cracking pressures may be used as long as they are above the shutoff valve set point for the device in the prior paragraph. For example, about 3 psi, 5 psi, 7 psi, or 10 psi above the maintained internal pressure. For example, 33 psi, 27 psi, 23 psi, 20 psi, 16 psi, 13 psi, 8, psi or 6 psi. When the pressure increases, this recycling valve opens and allows flow from the sterile side back to the feed side. To avoid backwards contamination, two additional check valves may be preferably placed in this line, which ensures water can only move in one direction. The high pressure check valve serves this purpose already, but the redundant valves are included to remove even small chances of reverse flow slip. The recycling valve acts as a pressure relief valve for the forward osmosis membrane module. In an embodiment, an automated recycling valve may be used in place of the pressure relief check valve(s), which would monitor the pressure of the product (lumen) side of the forward osmosis module and open when the pressure is high enough.

To ensure the best produced dialysate, an embodiment of the dialysate generator includes a bypass valve for flushing the system prior to collection. In a preferred embodiment, the dialysate generator produces dialysate at 1 L increments. When producing the dialysate, the first liter produced is not going to be at the correct concentration for patient use. During the first liter of production then, the bypass valve begins open and directs flow to bypass the collection reservoir, two-stroke piston, four-way valve, and an additional flow path is added just before the collection reservoir, at the device terminal port, to direct the first liter of produced dialysate to the feed waste discharge reservoir. An automated valve may be placed in this line to allow flow for the first 1 L of use, then close and allow regular flow for the remainder of dialysate generator use. Following the bypass valve on the alternate flow path line, check valves may be present to further prevent any back flow to the product collection.

In a broadly defined form, the device is an osmotically active medical solution generator, where particulate free water (potable or non-potable) is fed to one side of a forward osmosis membrane. A concentrate containing all of the necessary components of desired medical fluid, but significantly more concentrated than desired medical fluid is fed to the other side of the membrane. Water is pulled across the membrane due to the osmotic pressure difference and mixes with the concentrated fluid, producing a solution of the correct proportions.

In a more complex form, the device includes a prefilter for particulate removal. In the preferred arrangement, this prefilter is a 0.2 μm hollow fiber filter which removes all bacteria and protozoa, as well as any particulates. This filter enables the operator to use any portable or non-potable water source (with osmolality below that of desired solution), even those with particulates. An optional, and preferred adaptation adds an activated carbon (AC) column to the front of the system for organic and chloramine removal. AC is the preferred method for chloramine removal in water for hemodialysis systems per ISO 23500-2:2019. This filtration step also improves the efficiency of the device by removing osmolytes ahead of the forward osmosis membrane, creating a larger osmotic pressure difference at the membrane. An additional adaptation of the filtration train includes a sediment filter, which can be used with high-silt source waters. While the previous filtration trains can handle water with silt, it has been observed that high silt content can result in clogging of the filters. A sacrificial and disposable sediment filter, specifically designed for removing large particles prevents clogged filters, reduces overall system pressure drop, and further improves device performance. In another optional adaptation, an ion exchange resin is added to the front of the system, before the carbon column, to allow for use of saline water as a feed water source.

In one variation, the device includes a mechanism to precisely measure the produced volume of solution. To accurately produce a solution of the desired concentration, a precise volume must be measured, which has the proper concentration when mixed. In this embodiment, the device is non-powered, and therefore relies on an analog measurement system. In this preferred variation, the collection reservoir comprises a two-stroke piston reservoir (FIG. 12) for precisely measuring the produced volume of solution. This system consists of a piston and cylinder, also described as a two-stroke piston in this invention, and one or a series of valves (or a 4-way valve) which enable flow to enter and exit from either side of the cylinder. As the desired solution flows to one side of the cylinder, the piston is pushed through the cylinder and liquid on the other side is dispensed from the device. On the next production batch, the valve system can be used to switch the filling and exiting sides of the cylinder. In this way, each production batch dispenses the previous production batch, which alleviates any need for an operator to manually plunge the device. This series of positions is shown in FIGS. 14-19.

In a preferred configuration, the device also comprises an optional sediment filter. However, when operating with non-silty waters, removing the sediment filter is desired to provide the minimum system pressure drop. In this embodiment any water with osmolality below that of the desired solution is fed first to an activated carbon filter, which removes chloramines and organics. An additional configuration also comprises an ion exchange resin to use salty water as a feed water source. When operating with non-salty waters, removing this additional resin is desired. Water then flows into a 0.2 μm hollow fiber filter, which serves to sterilize the water (removes nearly all protozoa and bacteria) and remove any particulates. The now-potable water is fed to one side of the forward osmosis membrane. In this embodiment, a path allows for this water to flow through the feed side of the membrane and out to a discharge. This discharge path is equipped with an automatic valve, which can be turned to flush the feed side of the system. This improves system performance as the contaminants removed by the forward osmosis membrane become concentrated on the feed side of the membrane during production. This water has a higher osmotic potential, and therefore the osmotic differential is reduced. Clearing this old water out prior to producing a solution results in significant performance improvements. A preferred variation uses a manual or automated pump to introduce the concentrate to the forward osmosis membrane, allowing precise volume measurement of the introduced concentrate. The pump only allows for a specific volume of concentrate to be added to the system, and does not pump liquid across the forward osmosis membrane. The concentrate is stored in a large reservoir, which can hold enough concentrated solution to produce numerous batches of the desired medical solution, without requiring disconnection and reconnection. Minimizing disconnect/reconnect cycles improves operation and decreases potential for contamination.

This embodiment also includes a pressure relief recycle, which can return fluid from the high pressure, product side of the membrane to the feed side of the membrane. This recycle is included before the discharge valve to prevent leaking during transport. Due to construction methods, some forward osmosis membranes are not capable of operating at high pressures. The pressure relief can be tuned to actuate below the maximum operating pressure of a certain membrane, preventing damage. This relief is only actuated during high pressure events, which typically occur during the pre-run flush, and after a production batch. In this embodiment, the injection of concentrated solution draws water across the forward osmosis membrane where it is mixed with the concentrate and pushed into the piston and cylinder system described above. If the produced solution is a bicarbonate-based dialysate, this final bag would preferably contain a method to mix bicarbonate in post-production. This allows for longer storage of the product, as dialysate should be used soon after mixing bicarbonate due to precipitation reactions. In the preferred embodiment, when bicarbonate-based dialysates are desired, the concentrated dialysate injection consists of all the solution components, excluding the bicarbonate. Finally, in the preferred version of the device, a system is included on the final container fill line to allow sterile ion sampling of the produced solution.

A variation of the dialysate generator comprises a sterile reservoir valve and a backflush and sterilization reservoir. The reservoir contains a sterilant which can be introduced to the feed side of the forward osmosis membrane, allowing it to penetrate the membrane and sterilize the product side. In an embodiment, the sterilant is Minncare Sterilant, though equivalents may be used so long as they are biologic-free. In an embodiment, the concentrated sterilant is mixed with water in the backflush and sterilization reservoir, before the sterile reservoir valve is toggled to allow flow from the reservoir into the forward osmosis membrane. This flow path also may facilitate backflush of the prefilter. Over prolonged use, it is possible that particulate material will accumulate on the surface of the filter and lead to increased pressure drops across the filter. The filter can be cleaned by backflushing (flowing water from the clean side to the dirty side) to push particulate matter off the surface and refresh the filter. To backflush the system, clean, biologic-free water can be pushed or pumped from the backflush and sterilization reservoir through the prefilter by toggling the sterile reservoir valve. A sterile backflush valve is placed in line with the backflush flow path and is toggled to allow flow from the backflushing reservoir, through the prefilter, and directly to the discharge reservoir to dispose of the dirty backflushed water and avoid contaminating the carbon column. The backflush may be accomplished with a pump or by manually squeezing or manipulating the reservoir to produce a liquid flow through the prefilter. The sterilization may be accomplished with a pump or manual manipulation of the reservoir to produce a liquid flow through the prefilter. The valves are both directed to a normal operation flowpath to continue dialysate production.

Another variation of the dialysate generator comprises an acid reservoir, and an acid pump for post-production addition of an acid for pH adjustment. To produce finished dialysate, sodium bicarbonate needs to be added to the dialysate produced in the dialysate generator. Sodium bicarbonate increases the solution pH, so an acid such as hydrochloric acid also needs to be added to bring the pH back to the desired range. In an embodiment, acid is added automatically in line to the produced dialysate, and the collection reservoir or fillable bag comprises a second containment section for sodium bicarbonate, separated from the dialysate by a frangible seal that can be broken later and provide usable dialysate solution.

Any number of various optional transmitters, transducers, monitors, probes, sensors, detectors, or the like may be added in-line on the dialysate generator to improve performance and consistency of product. These optional components may measure metrics such as flow, pressure, analyte concentration, temperature, volume, and other changes in the system's internal environment at any point. The transducers may produce signals for automating pumps or valves in the system, or they may simply communicate the status of the system to a user for manual quality-checks.

While each valve and pump may be manual in some embodiments of the dialysate generator, it is preferred to automate the entire system. Automation decreases risk of human error, disconnect/connect contamination, delays, and required expertise for use. Though the dialysate generator is entirely automated, there is no power to pump liquid across the forward osmosis membrane, or transfer produced dialysate from the forward osmosis membrane to the collection reservoir. Optional pumps on the feed side of the dialysate generator, entering the first fluid side through the inlet to the forward osmosis membrane, do not generate greater than 5 psi of fluid pressure at the surface of the osmosis membrane. Without wishing to be bound by theory, this is a much lower fluid pressure than would be required to generate reverse osmosis. Even in automated embodiments of the dialysate generator, the dialysate generator does not use any external power source to produce medical-grade dialysate solution—batteries provide the required power for any pumps, valves, or transmitters and allows the dialysate to be man-portable in all embodiments. The dialysate generator weighs less than 50 pounds in the most complex embodiment with the most additional components, and preferably less than 31 pounds. In manually-operated embodiments, the dialysate generator weighs less than 31 pounds, preferably less than 10 pounds.

In one embodiment, a flow meter (1037) near the collection reservoir (1004) controls the product valve (1022), acting to shut off flow to the collection reservoir once 1 L of produced dialysate (1009) has flowed past the flow meter and into the collection reservoir. The product valve could also be controlled by an analyte transducer (1036), or a combination of the two sensors. In another embodiment, pressure and/or flow meters placed before and after the prefilter, or before and after the forward osmosis module, ensure that a certain pressure is maintained in the system and quickly detect any pressure spikes or drops across different components of the generator. Pressure spikes or drops may indicate when a backflush or sterilization should be run in some embodiments.

It is preferred to automate the dialysate generator to produce dialysate in 1 L increments, but using no external power source for the automation of valves or pumps, and the codes and signals throughout the device. It is possible for the entire dialysate generator to run manually, replacing pumps with syringes, hand pumps, or gravity-based flow designs. However, automating the system allows a user to push a single button and produce a desired amount of dialysate—preferably discarding the first liter of product, then collecting 1 L bags or vessels of dialysate, preferably with an acid additive, and preferably monitoring for pressure spikes and automatically redirecting flow or running sterilization or backflush pathways.

Example 1: a version of the device was used to measure the TOC penetration in the device. The first three elements are the filtration train, consisting of the carbon column, microfilter, and FO module. In this example, water was fed from a large reservoir, mounted above the unit. A 1 L IV bag and load cell were used, to measure the water in 1 L increments. The water was fed to this IV bag from the FO module, and was discharged from the IV bag to a discharge reservoir. An automated system using 4 valves, a pump, a load cell, and an LED screen were implemented using a micro controller. The first valve was located on the feed discharge line, exiting from the bottom tube (lumen) side of the FO module. This valve was used to control flush volume, and was fed to a discharge. The next two valves were used to control the inlet and outlet of the IV bag, so that it could be filled without draining, and drained only to a discharge reservoir, and not back to the system. The last valve was used to block the pressure recycle during the injection, so that no injection was pushed through the recycle. The load cell was used to measure the amount of liquid filling into the IV bag. Finally, the pump was used to replace the injection system. A reservoir of injection concentrate was fed to the pump, and the pump was programmed to inject at 300 mL/min for 10 s, resulting in a 50 mL injection. The injection concentrate used for this example was a mixture of sodium chloride, calcium chloride, and potassium chloride, which was mixed to form an osmotically similar solution to the typical injection concentrate. Carbon containing compounds were eliminated to efficiently measure TOC removal in the system, without interference from internal carbon sources. The system was run using both tap water, and water from a local river (Clear Creek, collected in Wheat Ridge, CO and representing a mountain surface drainage waterway in a suburban runoff area) which was filtered to remove silt prior to use in the testing apparatus. Operation consisted of 4 phases, which were all automated to allow a long-term experiment. Phase one was a 1-minute system flush where feed water was allowed to run through the full filtration train, and out of the FO module on the feed side to the system discharge. This step cleaned the module of any concentrated dirty water from the previous run. Phase 2 was the injection step, where the discharge valve closed, the valve to the fill IV bag opened, the valve on the recycle line closed, and the pump was started to push 50 mL of injection into the system. Phase 3 was the filling phase, where the fill valve was left open and the system ran water through the filtration train and across the FO membrane to fill into the IV bag. The IV weight was measured, and the system terminated the filling step at 1000 g (1 Liter). Phase 4 was the fill discharge stage, where the IV fill valve was closed, and the IV drain valve was opened. The system was designed to drain for 1.5 minutes. Samples were drawn from the IV drain line, prior to entering the discharge, and TOC was measured using a Sievers M9 TOC analyzer. Results of this testing are shown in FIG. 12. The TOC was efficiently removed from both the tap (black squares) and natural water (black and white triangles), with no signs of breakthrough for over 50 bags of production. The inlet TOC for the tap water was 1.35 ppm for this test, while the inlet TOC of the filtered clear creek water was around 8.8 ppm. In both cases, the TOC was eliminated from the feed water, and water well below the water for injection (WFI) target (solid black line) was produced.

Figure 21:
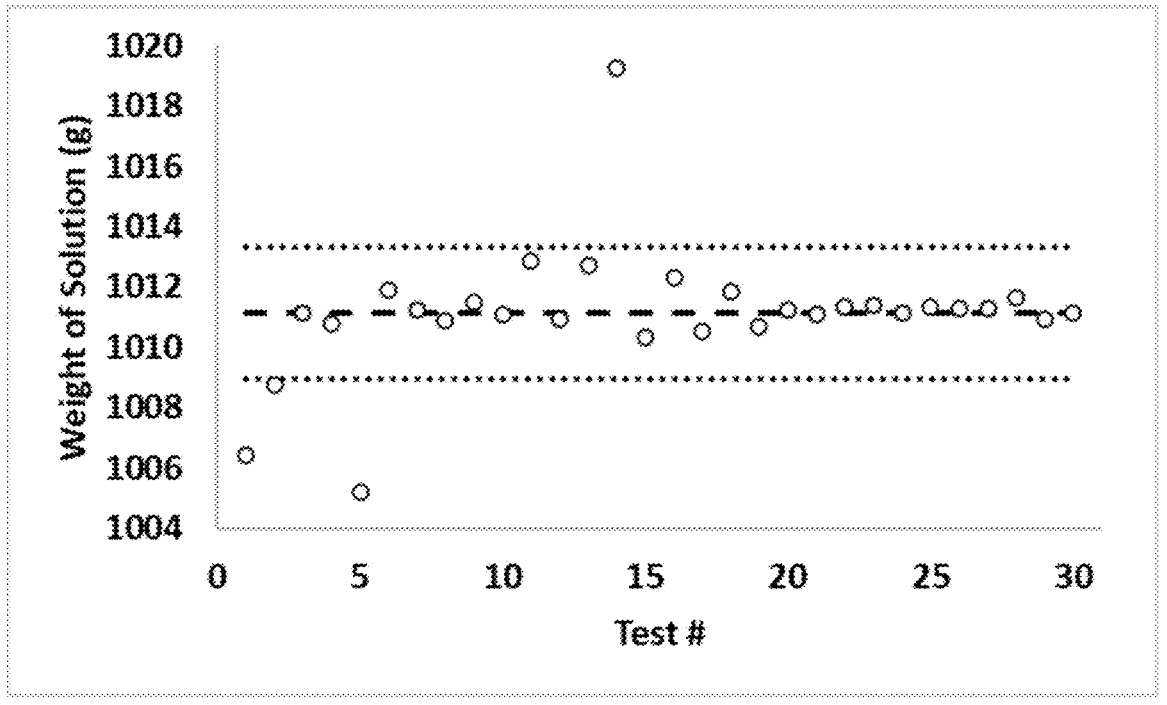
FIG. 21: Weight of solution for 30 separate tests.

Example 2: a version of the device was used to evaluate the piston and cylinder filling mechanism. The system was run to produce dialysate over several days of testing, and the final weight of the produced solution was measured as a proxy for volume measurement. The system was run in the standard operating method, consisting of a flushing step, an injection step, and a filling step in which the previous runs solution is dispensed by the piston. Injection solutions were altered each day as this testing was also used to examine ion concentrations. Solutions were filled into 1 L bottles, which were weighed before and after filling to determine the filled weight. The results of this testing are shown in FIG. 21. A total of 30 tests were run across 5 days, with an average of 1011.1 g fill weights and an extremely tight standard deviation of 2.2 grams, or 0.2% of the target weight of 1007 g. This target is based on the density of dialysate vs water.

Figure 22:
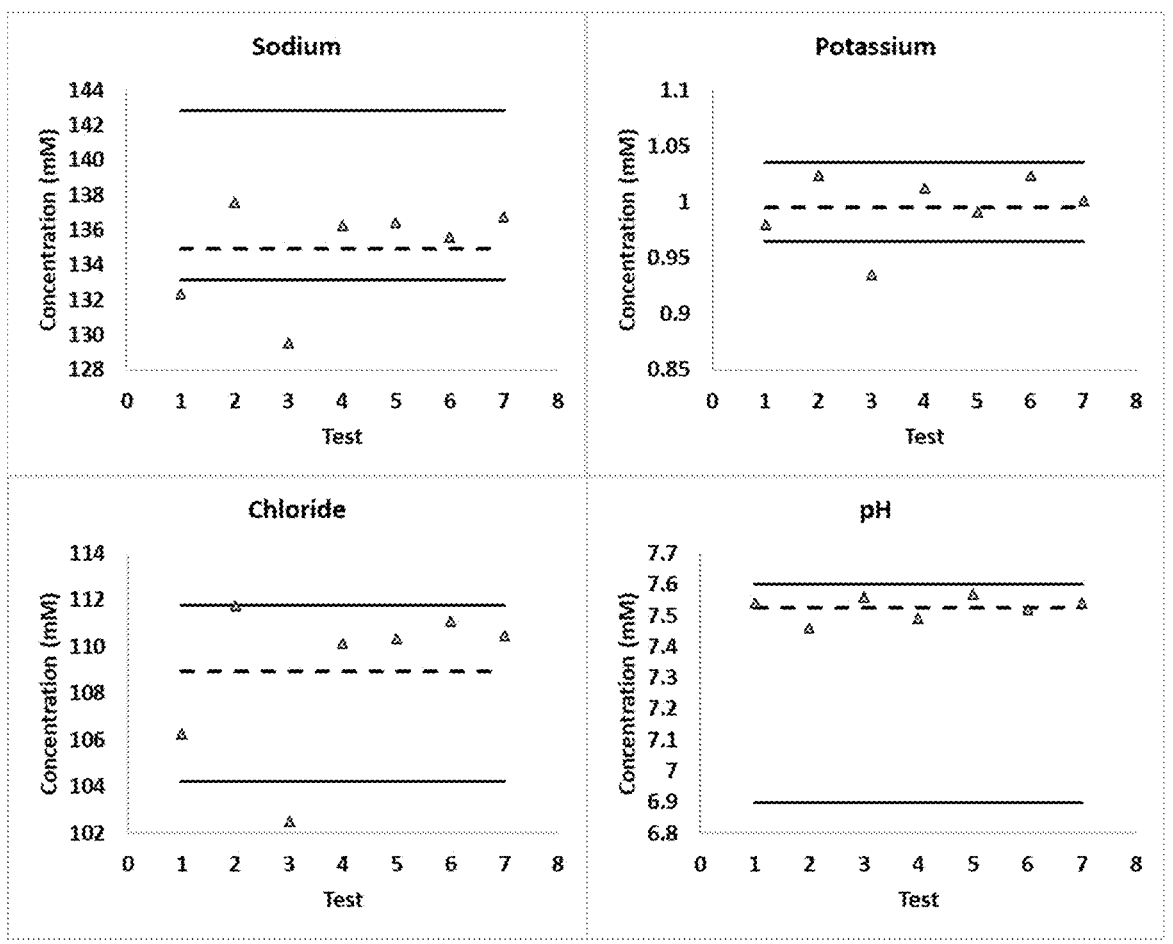
FIG. 22: Sodium, potassium, chloride, and pH concentration of dialysate produced by the generator.

Example 3: a version of the device, the same device used in example 2, was used to test the ability of the Dialysate Generator to produce dialysate. A 1 L solution of injection concentrate was produced, containing 188.01 g NaCl, 2.2598 g KCl, 6.5205 g CaCl2, 1.4105 g MgCl, 28.4502 g Glucose, 7.5 mL glacial acetic acid. This solution was mixed by adding powdered components to a 1 L volumetric flask, followed by addition of water. Glacial acetic was added after water addition, and the solution was then topped off to 1 L with DI water. The solution was added to a 1 L reservoir, which was connected into the system at the injection concentrate connection. The system was run as normal, with a 90 second flush, followed by injection of 40 mL of concentrate to the bottom of the module. Each run was filled into the piston/cylinder system, and the fluid collected was of the previous run. 500 mL aliquots of each produced solution were mixed with 1.34 g of sodium bicarbonate, and the resulting solution was analyzed for pH using a pH meter, and Na, K, and Cl using an EasyLyte Expand table-top analyzer. The results of this testing are in FIG. 22, demonstrating dialysate production within the desired ion and pH range. The target ranges are outlined by solid black lines, while the dotted line gives the average of the tests shown by triangles.

Figure 23:
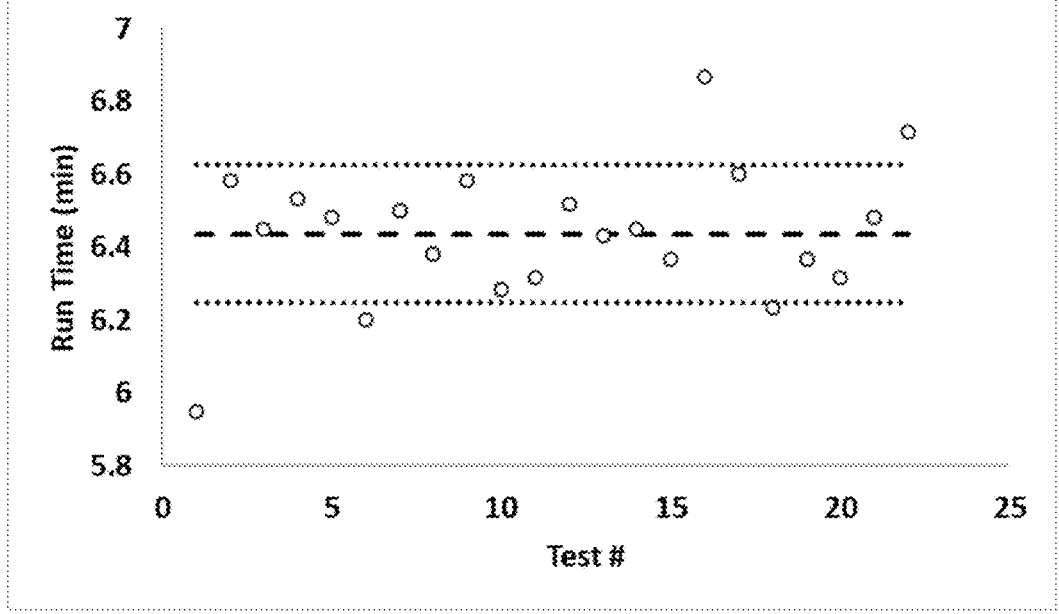
FIG. 23: Run time per test.

Example 4: the same device used in example 2 and 3 was also used to look at the production run time for dialysate. Run time is defined as the total time needed to produce 1 L of dialysate, and includes the flushing time in addition to the time required to fill the 1 L cylinder. The flushing time was examined over several days of testing, using the same production method and system as outlined in example 2 and 3. Each flush for this testing was 90 seconds. The results of this test are shown in FIG. 23, showing an average run-time of 6.4 minutes (6:26), with a standard deviation of 11.4 seconds. The full range of this testing covers production times from 5:57 to 6:52, which equates to a production rate of roughly 8-10 L of dialysate/hour.

Example 5: In this example, a version of the device was used to evaluate the sterility of produced dialysate solutions. To demonstrate sterility of the core device, solutions were produced directly into sterile IV bags from the FO module (the filling mechanism was not included). A manual valve was placed on the fill line, and the runs were determined to be complete when the bags visually appeared to be at 1 L of dialysate. A needleless connector was used as the fill line termination component, to maintain sterility. First, a solution of 1% Minncare® cold sterilant was produced by mixing 1980 mL of DI water with 20 mL of Minncare® concentrate. Minncare® Cold Sterilant is a peracetic acid solution developed for use on reverse osmosis (RO) membranes and their associated distribution systems. Minncare® is 22% hydrogen peroxide, 9% acetic acid, 5% peroxyacetic acid, and 1% of a proprietary stabilizer (balance of mass is water). A sterilizing filter (0.2 μm) was placed in line prior to the injection system, to remove the need to sterilize the injection solution. A peristaltic pump was attached to the other side of the sterilizing filter, and a was fed with the 1% Minncare® solution. A discharge line was placed from the fill line to a discharge. Minncare® was pumped through the system. 3 times during the Minncare® pumping, the pump was turned off, the outlet was closed, the feed discharge (bottom of the FO module) was opened, and Minncare® was manually pump through the recycle using the syringe. When nearly all the Minncare® had been used (with enough left to ensure no air was pumped to the system), the discharge line was disconnected from the fill line, the pump was disconnected, and the system was allowed to sit for 3 hours (minimum contact time is 36 minutes).

A solution of concentrated dialysate was produced using a similar formulation as Example 3. Connectors made of two male luers, and a small (~5" section of $\frac{1}{16}$" tubing) were made and autoclaved. Luers are a connection widely understood in the art and originally invented and patented by Hermann Wülfing Lüer in the 19$^{th}$ Century. There are modern trademarked variations of luers, such as LUER-LOK®. Individually packaged sterile needles (16 gauge) were procured. Individually packaged, 1 L sterile IV bags with septa ports were procured. The work area was cleaned, and sterile procedure was followed, using gloves which were periodically rinsed with isopropyl alcohol.

After the 3 hours had passed, the system was flushed of Minncare®. Flushing was completed by running the system as normal, using the concentrated dialysate injection. An autoclaved connector, and sterile needle were attached to the needleless connector on the fill port, which was swabbed with isopropyl prior to connection. The needle cap was removed and an IV bag was connected by pressing the needle through the septa. The system was flushed through the feed side flush valve for 1 minute. While flushing, an IV bag containing the dialysate concentrate was connected to the sterile filter on the injection line. 40 mL of injection was drawn into the syringe. After the flush, the feed flush valve was closed, the fill valve was opened to the IV bag, and the syringe was injected. The IV bag was monitored until it appeared that 1 L of fluid had been dispensed, at which point the fill valve was closed. The IV bag was removed from the system, and the needle recapped. The IV bag was then sampled for the presence of Minncare® using Minncare® test strips. A new IV bag was placed on the needle/connector. This process was repeated until the produced IV bag read 0 ppm of Minncare®, which turned out to be 5 L of flushing (5 production bags).

Once the system had been fully flushed of Minncare®, the autoclaved connector and needle used for flushing were removed. The needleless fill connector was swabbed with isopropyl alcohol, and a new autoclaved connector and needle were attached. A fresh, sterile IV was removed from its packaging and attached to the needle via the septa port. Dialysate was produced following the same procedure as the flushing steps. When the bag was observed to be finished, the needle was removed and the connector was disconnected from the fill line needleless connector. This process was repeated until 6 IV bags of dialysate had been produced.

The IV bags were weighed to evaluate how close to 1 L the production was. For anaerobic and aerobic growth samples, test tubes with 10 mL of growth media were procured or produced. For aerobic growth a fluid thioglycolate media (FTG) was produced following USP regulations. For anaerobic growth tryptic soy broth (TSB) was precured from Hardy Diagnostics. Each IV bag was sampled twice, once for aerobic and once for anaerobic evaluation. A 22-gauge needle and 1 mL sterile syringe were used for each sampling. The septa-port of the IV bag was swabbed before each needle insertion. The IV was hung, and the needle was inserted from below the IV bag through the septa. Liquid was drawn into the syringe, and all air was removed. Then exactly 1 mL was measured and was dispensed into the growth media for that specific sample. The septa of the media tubes were swabbed prior to piercing with the sample needle. In addition to the IV bag samples, control samples of the source water were taken from the source bag and evaluated for both aerobic and anaerobic growth. The aerobic (FTG) samples were incubated for 2 weeks at 22.5±2.5° C., while the anaerobic (TSB) samples were incubated for 2 weeks at 32.5±2.5° C., following USP sterility standards for parenteral drugs. This standard is above and beyond what is required for water for hemodialysis through ISO 23500-5: 2019.

After 2 weeks, none of the dialysate samples showed any growth, while both the anaerobic and aerobic controls showed growth, indicating successful production of sterile solutions.

Figure 24:
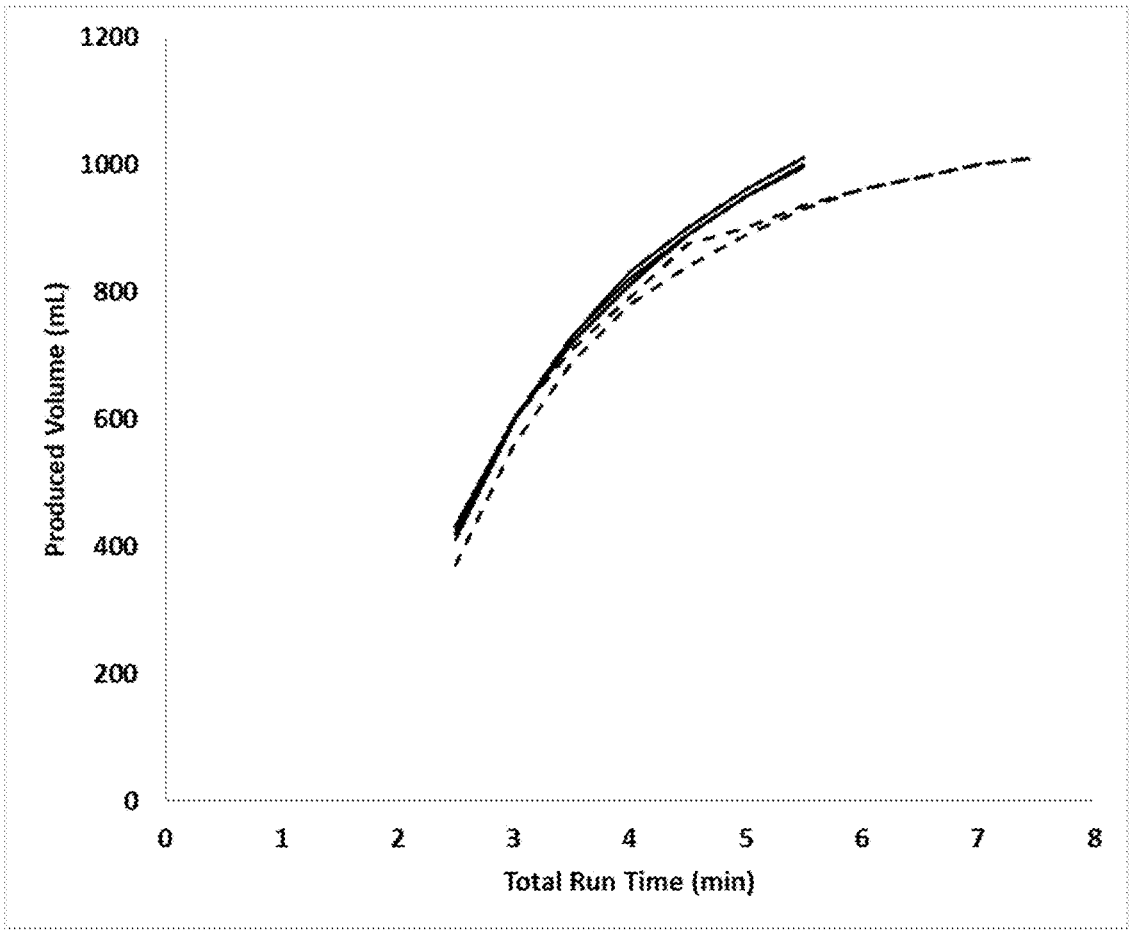
FIG. 24: Produced dialysate volume vs. run time (counter current vs. concurrent). The solid lines are for the counter current tests.

Example 6: in this example a cross flow version of the system shown was compared to a co-current version. In this test an electrolyte solution osmotically similar to dialysate was used containing sodium chloride, potassium chloride, calcium chloride dihydrate, and sodium lactate. Both systems were run with 1.5 minute flush times and a 50 mL injection of the concentrate. The produced volume was measured at 30 second intervals during the run, with the run finishing at ~1010 mL. The results are shown in FIG. 24 with two replicate tests of the co-current (dotted lines) and three replicates of the counter-current (solid lines) system. The tests are shown over the full system run time, which includes the 1.5 minute flush, and measurements started at 2.5 minutes. This testing demonstrated the clear impact from the module orientation change. Both systems begin at a similar rate, but the co-current system tails off towards the end and begins to fill much slower. This is consistent with our hypothesis that the counter-current system is better at retaining the highly concentrated injection, thus maximizing the osmotic differential for longer.

Although the present invention has been described in considerable detail with reference to certain preferred versions thereof, other versions are possible. Therefore, the spirit and scope of the appended claims should not be limited to the description of the preferred versions contained herein, except where required by Law.

The reader's attention is directed to all references which are filed concurrently with this specification and which are incorporated herein by reference.

All the features in this specification (including any accompanying claims, abstract, and drawings) may be replaced by alternative features serving the same, equivalent or similar purpose, unless expressly stated otherwise. Thus, unless expressly stated otherwise, each feature disclosed in one example only of a generic series of equivalent of similar features.

What is claimed is:

1. A portable dialysate generator, comprising:
   a) a forward osmosis membrane module;
   b) a concentrated aqueous salt solution reservoir;
   c) a non-sterile water feedstock inlet;
   d) a collection reservoir;
   e) a sterile dialysate collection reservoir; and
   f) a four-way valve;
   wherein, the forward osmosis membrane module has a first fluid side and a second fluid side, the first fluid side and the second fluid side being separated by an osmosis membrane;
   wherein, the non-sterile water feedstock inlet is operably connected to, and in fluid communication with the first fluid side of the forward osmosis membrane module;
   wherein, the concentrated aqueous salt solution reservoir is operably connected to, and in fluid communication with the second fluid side of the forward osmosis membrane module;

wherein, the collection reservoir is operably connected to, and in fluid communication with the second fluid side of the forward osmosis membrane module;

wherein, the portable dialysate generator does not have an electric-powered pump to move a fluid across the osmosis membrane;

wherein, the portable dialysate generator is man-portable;

wherein the non-sterile water feedstock inlet and the concentrated aqueous salt solution reservoir are operably connected to the forward osmosis membrane module in a counter-concurrent configuration;

wherein the sterile dialysate collection reservoir is connected to and in fluid communication with the second fluid side of the forward osmosis membrane module;

wherein the sterile dialysate collection reservoir is fillable by a produced dialysate from the second fluid side of the forward osmosis membrane module, and wherein there is no electric-powered pump to move the produced dialysate from the forward osmosis membrane module to the sterile dialysate collection reservoir;

wherein the sterile dialysate collection reservoir is either a flexible and fillable bag or a movable piston, and wherein the sterile dialysate collection reservoir is operably connected to the forward osmosis membrane module so excess fluid volume produced in the forward osmosis membrane module can fill the sterile dialysate collection reservoir;

wherein the collection reservoir comprises a two-stroke piston with a first collection reservoir side and a second collection reservoir side;

wherein the four-way valve is operably connected to and in fluid communication with the forward osmosis membrane module and the collection reservoir; and, wherein, the four-way valve directs fluid communication from the forward osmosis membrane module to the first collection reservoir side or to the second collection reservoir side.

2. The portable dialysate generator of claim 1, wherein, the portable dialysate generator does not have an electric-powered pump to move a non-sterile water feedstock through the non-sterile water feedstock inlet into the forward osmosis membrane module; and, wherein, the portable dialysate generator does not have an electric-powered pump to move a concentrated aqueous salt solution from the concentrated aqueous salt solution reservoir into the forward osmosis membrane module.

3. The portable dialysate generator of claim 1, further comprising a non-sterile water feedstock reservoir operably connected to and in fluid communication with the non-sterile water feedstock inlet, wherein, the non-sterile water feedstock source is mounted above the forward osmosis membrane module, operably allowing gravity-feeding of fluid from the non-sterile water feedstock source into the forward osmosis membrane module.

4. The portable dialysate generator of claim 1, further comprising a non-sterile water feedstock source and a feed pump, wherein the feed pump is connected between and in fluid communication with the non-sterile water feedstock source and the non-sterile water feedstock inlet, operably allowing on-demand pumping of fluid from the non-sterile water feedstock source into the forward osmosis membrane module.

5. The portable dialysate generator of claim 1, further comprising an injection concentrate pump, wherein, the injection concentrate pump is connected between the concentrated aqueous salt solution reservoir and the forward osmosis membrane module, and is operably connected to and in fluid communication with the concentrated aqueous salt solution reservoir and the forward osmosis membrane module, operably allowing on-demand pumping of fluid from the concentrated aqueous salt solution reservoir into the forward osmosis membrane module.

6. The portable dialysate generator of claim 1, further comprising:

g) a final dialysate product collection reservoir;

wherein, the two-stroke piston is operably connected to the four-way valve and the final dialysate product collection reservoir such that when the four-way valve is positioned so that excess fluid volume from the forward osmosis membrane module is directed to the first collection reservoir side, the produced dialysate in the second collection reservoir is dispelled into the final dialysate product collection reservoir; and, wherein, the two-stroke piston is operably connected to the four-way valve and the final dialysate product collection reservoir such that when the four-way valve is positioned so that excess fluid volume from the forward osmosis membrane module is directed to the second collection reservoir side, the produced dialysate in the first collection reservoir is dispelled into the final dialysate product collection reservoir.

7. The portable dialysate generator of claim 6, wherein the final dialysate product collection reservoir comprises a bag reservoir, further comprising a first compartment and a second compartment, wherein the first compartment and the second compartment are separated by a frangible seal, wherein the produced dialysate is dispelled into the first compartment, and wherein an additive is stored, either as a solid or liquid, in the second compartment.

8. The portable dialysate generator of claim 1, further comprising at least one of an microfilter, a particle pre-filter, or an activated carbon filter operably connected to and in fluid communication between the non-sterile water feedstock source and the non-sterile water feedstock inlet.

9. The portable dialysate generator of claim 8, further comprising an ion exchange resin operably connected to and in fluid communication between the non-sterile water feedstock source and the at least one of the microfilter, the particle pre-filter, or the activated carbon filter.

10. The portable dialysate generator of claim 8, further comprising:

h) a backflush and sterilization reservoir; and, i) a sterilization pump;

wherein, the backflush and sterilization reservoir is operably connected to and in fluid communication with the first fluid side of the forward osmosis membrane module;

wherein, the sterilization pump is operably connected to and in fluid communication between the backflush and sterilization reservoir and the forward osmosis membrane module; and, wherein, the sterilization pump operably allows on-demand pumping of fluid from the backflush and sterilization reservoir into the forward osmosis membrane module.

11. The portable dialysate generator of claim 10, wherein the portable dialysate generator comprises a particle pre-filer, and wherein the backflush and sterilzation reservoir is further operably connected to and in fluid communication with the particle pre-filter.

12. The portable dialysate generator of claim 1, further comprising:

j) an acid reservoir; and, k) an acid pump;

wherein, the acid reservoir is operably connected to and in fluid communication between the forward osmosis membrane module and the sterile dialysate collection reservoir;

wherein, the acid pump is operably connected to and in fluid communication between the acid reservoir and the sterile dialysate collection reservoir;

wherein, the acid pump allows for on-demand pumping of fluid from the acid reservoir to the produced dialysate from the forward osmosis membrane module before entering the sterile dialysate collection reservoir; and, wherein, the acid pump does not move fluid from the forward osmosis membrane module to the sterile dialysate collection reservoir.

13. The portable dialysate generator of claim 1, further comprising a pressure relief valve connected to and in fluid communication with the second fluid side of the forward osmosis membrane module.

14. The portable dialysate generator of claim 13, wherein the pressure relief valve is further connected to an in fluid communication with the first fluid side of the forward osmosis membrane module, allowing flow from the second fluid side to the first fluid side to relieve pressure.

15. The portable dialysate generator of claim 1, further comprising a bypass valve and a discharge reservoir, wherein the bypass valve is operably connected and in fluid communication with the second fluid side of the forward osmosis membrane module and the discharge reservoir.

16. A portable dialysate generator, comprising:
a) a forward osmosis membrane module;
b) a concentrated aqueous salt solution reservoir;
c) a non-sterile water feedstock inlet;
d) a collection reservoir; and
e) a sterile dialysate collection reservoir;
f) a four-way valve;
wherein, the forward osmosis membrane module has a first fluid side and a second fluid side, the first fluid side and the second fluid side being separated by an osmosis membrane;
wherein, the non-sterile water feedstock inlet is operably connected to, and in fluid communication with the first fluid side of the forward osmosis membrane module;
wherein, the concentrated aqueous salt solution reservoir is operably connected to, and in fluid communication with the second fluid side of the forward osmosis membrane module;
wherein, the collection reservoir is operably connected to, and in fluid communication with the second fluid side of the forward osmosis membrane module;
wherein, the portable dialysate generator does not have an electric-powered pump that generates more than 5 psi for fluid pressure;
wherein, the portable dialysate generator is man-portable;
wherein the non-sterile water feedstock inlet and the concentrated aqueous salt solution reservoir are operably connected to the forward osmosis membrane module in a counter-concurrent configuration
wherein the sterile dialysate collection reservoir is connected to and in fluid communication with the second fluid side of the forward osmosis membrane module
wherein the sterile dialysate collection reservoir is fillable by a produced dialysate from the second fluid side of the forward osmosis membrane module, and wherein there is
no electric-powered pump to move the produced dialysate from the forward osmosis membrane module to the sterile dialysate collection reservoir;

wherein the sterile dialysate collection reservoir is either a flexible and fillable bag or a movable piston, and wherein the sterile dialysate collection reservoir is operably connected to the forward osmosis membrane module so excess fluid volume produced
in the forward osmosis membrane module can fill the sterile dialysate collection reservoir
wherein the collection reservoir comprises a two-stroke piston with a first collection reservoir side and a second collection reservoir side;
wherein the four-way valve is operably connected to and in fluid communication with the forward osmosis membrane module and the collection reservoir; and,
wherein, the four-way valve directs fluid communication from the forward osmosis membrane module to the first collection reservoir side or to the second collection reservoir side.

17. The portable dialysate generator of claim 16, wherein, the portable dialysate generator does not have an electric-powered pump to move a non-sterile water feedstock through the non-sterile water feedstock inlet into the forward osmosis membrane module; and,
wherein, the portable dialysate generator does not have an electric-powered pump to move a concentrated aqueous salt solution from the concentrated aqueous salt solution reservoir into the forward osmosis membrane module.

18. The portable dialysate generator of claim 16, further comprising a non-sterile water feedstock reservoir operably connected to and in fluid communication with the non-sterile water feedstock inlet, wherein, the non-sterile water feedstock source is mounted above the forward osmosis membrane module, operably allowing gravity-feeding of fluid from the non-sterile water feedstock source into the forward osmosis membrane module.

19. The portable dialysate generator of claim 16, further comprising a non-sterile water feedstock source and a feed pump, wherein the feed pump is connected between and in fluid communication with the non-sterile water feedstock source and the non-sterile water feedstock inlet, operably allowing on-demand pumping of fluid from the non-sterile water feedstock source into the forward osmosis membrane module.

20. The portable dialysate generator of claim 16, further comprising an injection concentrate pump, wherein, the injection concentrate pump is connected between the concentrated aqueous salt solution reservoir and the forward osmosis membrane module, and is operably connected to and in fluid communication with the concentrated aqueous salt solution reservoir and the forward osmosis membrane module, operably allowing on-demand pumping of fluid from the concentrated aqueous salt solution reservoir into the forward osmosis membrane module.

21. The portable dialysate generator of claim 16, further comprising:
h) a final dialysate product collection reservoir;
wherein, the two-stroke piston is operably connected to the four-way valve and the final dialysate product collection reservoir such that when the four-way valve is positioned so that excess fluid volume from the forward osmosis membrane module is directed to the first collection reservoir side, the produced dialysate in the second collection reservoir is dispelled into the final dialysate product collection reservoir; and,
wherein, the two-stroke piston is operably connected to the four-way valve and the final dialysate product collection reservoir such that when the four-way valve is positioned so that excess fluid volume from the forward osmosis membrane module is directed to the second collection reservoir side, the produced dialysate in the first collection reservoir is dispelled into the final dialysate product collection reservoir.

22. The portable dialysate generator of claim 21, wherein the final dialysate product collection reservoir comprises a bag reservoir with a first compartment and a second compartment, wherein the first compartment and the second compartment are separated by a frangible seal, wherein the produced dialysate is dispelled into the first compartment, and wherein an additive is stored, either as a solid or liquid, in the second compartment.

23. The portable dialysate generator of claim 16, further comprising at least one of an microfilter, a particle pre-filter, or an activated carbon filter operably connected to and in fluid communication between the non-sterile water feedstock source and the non-sterile water feedstock inlet.

24. The portable dialysate generator of claim 23, further comprising an ion exchange resin operably connected to and in fluid communication between the non-sterile water feedstock source and the at least one of the microfilter, the particle pre-filter, or the activated carbon filter.

25. The portable dialysate generator of claim 23, further comprising:

j) a backflush and sterilization reservoir; and, k) a sterilization pump;

wherein, the backflush and sterilization reservoir is operably connected to and in fluid communication with the first fluid side of the forward osmosis membrane module;

wherein, the sterilization pump is operably connected to and in fluid communication between the backflush and sterilization reservoir and the forward osmosis membrane module; and, wherein, the sterilization pump operably allows on-demand pumping of fluid from the backflush and sterilization reservoir into the forward osmosis membrane module.

26. The portable dialysate generator of claim 25, wherein the portable dialysate generator comprises a particle pre-filter, and wherein the backflush and sterilization reservoir is further operably connected to and in fluid communication with the particle pre-filter.

27. The portable dialysate generator of claim 16, further comprising:

l) an acid reservoir; and, m) an acid pump;

wherein, the acid reservoir is operably connected to and in fluid communication between the forward osmosis membrane module and the sterile dialysate collection reservoir;

wherein, the acid pump is operably connected to and in fluid communication between the acid reservoir and the sterile dialysate collection reservoir;

wherein, the acid pump allows for on-demand pumping of fluid from the acid reservoir to the produced dialysate from the forward osmosis membrane module before entering the sterile dialysate collection reservoir; and, wherein, the acid pump does not move fluid from the forward osmosis membrane module to the sterile dialysate collection reservoir.

28. The portable dialysate generator of claim 16, further comprising a pressure relief valve connected to and in fluid communication with the second fluid side of the forward osmosis membrane module.

29. The portable dialysate generator of claim 28, wherein the pressure relief valve is further connected to an in fluid communication with the first fluid side of the forward osmosis membrane module, allowing flow from the second fluid side to the first fluid side to relieve pressure.

30. The portable dialysate generator of claim 16, further comprising a bypass valve and a discharge reservoir, wherein the bypass valve is operably connected and in fluid communication with the second fluid side of the forward osmosis membrane module and the discharge reservoir.

* * * * *